US011735322B2

(12) United States Patent
Zhang et al.

(10) Patent No.: US 11,735,322 B2
(45) Date of Patent: Aug. 22, 2023

(54) SYSTEMS AND METHODS FOR OSSIFICATION CENTER DETECTION AND BONE AGE ASSESSMENT

(71) Applicant: SHANGHAI UNITED IMAGING INTELLIGENCE CO., LTD., Shanghai (CN)

(72) Inventors: Minqing Zhang, Shanghai (CN); Qin Liu, Houston, TX (US); Dijia Wu, Shanghai (CN); Yiqiang Zhan, Shanghai (CN); Xiang Sean Zhou, Shanghai (CN)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 0 days.

(21) Appl. No.: 17/806,269

(22) Filed: Jun. 9, 2022

(65) Prior Publication Data

US 2022/0309663 A1 Sep. 29, 2022

Related U.S. Application Data

(63) Continuation of application No. 16/729,302, filed on Dec. 28, 2019, now Pat. No. 11,367,181.

(30) Foreign Application Priority Data

Dec. 29, 2018 (CN) .......................... 201811632931.8
Mar. 6, 2019 (CN) .......................... 201910168616.2
Sep. 19, 2019 (CN) .......................... 201910886148.2

(51) Int. Cl.
*G16H 50/50* (2018.01)
*G06T 7/00* (2017.01)
(Continued)

(52) U.S. Cl.
CPC .......... *G16H 50/50* (2018.01); *G06T 3/4007* (2013.01); *G06T 7/0012* (2013.01); *G06T 7/11* (2017.01);
(Continued)

(58) Field of Classification Search
CPC ........ G16H 50/50; G16H 10/60; G16H 30/00; G16H 30/40; G16H 50/30; G06T 3/4007;
(Continued)

(56) References Cited

U.S. PATENT DOCUMENTS 7,956,894 B2 6/2011 Akers et al.
2003/0065264 A1* 4/2003 Tsoref .................. A61B 8/0875
600/442
(Continued)

FOREIGN PATENT DOCUMENTS

CN 107590510 A 1/2018
CN 107591200 A * 1/2018
(Continued)

OTHER PUBLICATIONS

Cavallo, F. "Evaluaion of Bone Age in Children: A Mini-Review" Frontiers in Pediatrics vol. 9, Article 580314 Mar. 12, 2021.*
(Continued)

*Primary Examiner* — Mia M Thomas
(74) *Attorney, Agent, or Firm* — Metis IP LLC

(57) ABSTRACT

Systems and methods for ossification center detection (OCD) and bone age assessment (BAA) may be provided. The method may include obtaining a bone age image of a subject. The method may include generating a normalized bone age image by preprocessing the bone age image. The method may include determining, based on the normalized bone age image, positions of a plurality of ossification centers using an ossification center localization (OCL) model. The method may include estimating, based on the
(Continued)

normalized bone age image and information related to the positions of the plurality of ossification centers, a bone age of the subject using a bone age assessment (BAA) model.

20 Claims, 26 Drawing Sheets

(51) Int. Cl.
*G06T 7/73* (2017.01)
*G06T 3/40* (2006.01)
*G06T 7/11* (2017.01)
*G16H 10/60* (2018.01)
*G16H 30/00* (2018.01)
*G06V 10/143* (2022.01)
*G06V 40/10* (2022.01)

(52) U.S. Cl.
CPC .............. *G06T 7/74* (2017.01); *G06V 10/143* (2022.01); *G06V 40/107* (2022.01); *G16H 10/60* (2018.01); *G16H 30/00* (2018.01); *G06T 2207/20084* (2013.01); *G06T 2207/20104* (2013.01); *G06T 2207/30008* (2013.01)

(58) Field of Classification Search
CPC . G06T 7/0012; G06T 7/11; G06T 7/74; G06T 2207/20084; G06T 2207/20104; G06T 2207/30008; G06T 7/143; G06T 7/73; G06V 10/143; G06V 40/107; A61B 5/055; A61B 5/7203; A61B 5/4504
See application file for complete search history.

(56) References Cited

U.S. PATENT DOCUMENTS

| | | | |
|---|---|---|---|
| 2007/0274442 A1* | 11/2007 | Gregory | A61B 6/482 600/407 |
| 2009/0105953 A1 | 4/2009 | Thodberg | |
| 2014/0081146 A1 | 3/2014 | Keim et al. | |
| 2015/0066539 A1 | 3/2015 | Sheffer et al. | |
| 2017/0032518 A1* | 2/2017 | Behrooz | G06T 7/187 |
| 2017/0211070 A1 | 7/2017 | Hino et al. | |
| 2018/0061054 A1 | 3/2018 | Abraham et al. | |
| 2018/0232603 A1 | 8/2018 | Shim et al. | |
| 2018/0247020 A1* | 8/2018 | Itu | G16H 10/60 |
| 2018/0338740 A1* | 11/2018 | Behrooz | G06T 7/187 |
| 2019/0005360 A1 | 1/2019 | Heide | |
| 2019/0206052 A1 | 7/2019 | Hu et al. | |
| 2020/0020097 A1 | 1/2020 | Do et al. | |
| 2020/0211187 A1* | 7/2020 | Zhang | A61B 5/4504 |
| 2020/0253942 A1 | 8/2020 | Era et al. | |
| 2020/0372633 A1 | 11/2020 | Lee et al. | |
| 2021/0034905 A1 | 2/2021 | Lee | |
| 2021/0042921 A1 | 2/2021 | Tsai et al. | |
| 2021/0142477 A1 | 5/2021 | Tsai et al. | |
| 2021/0204895 A1 | 7/2021 | Mo | |
| 2022/0401221 A1* | 12/2022 | Chaoui | A61B 34/10 |

FOREIGN PATENT DOCUMENTS

| | | | | |
|---|---|---|---|---|
| CN | 107591200 A | | 1/2018 | |
| CN | 107767376 A | * | 3/2018 | ........... G06T 7/0012 |
| CN | 107767376 A | | 3/2018 | |
| CN | 107895367 A | | 4/2018 | |
| CN | 108056786 A | * | 5/2018 | ............. A61B 6/505 |
| CN | 108056786 A | | 5/2018 | |
| CN | 108334899 A | | 7/2018 | |
| CN | 108334899 A | * | 7/2018 | |
| CN | 109035252 A | | 12/2018 | |
| CN | 109146879 A | | 1/2019 | |
| CN | 109215013 A | | 1/2019 | |
| CN | 109271992 A | | 1/2019 | |
| CN | 109741260 A | | 5/2019 | |
| CN | 109754403 A | | 5/2019 | |
| CN | 109816721 A | | 5/2019 | |
| CN | 109949223 A | | 6/2019 | |
| CN | 109949280 A | | 6/2019 | |
| CN | 110120033 A | | 8/2019 | |
| KR | 20080065078 A | | 7/2008 | |

OTHER PUBLICATIONS

International Search Report in PCT/CN02019/129636 dated Mar. 27, 2020, 5 pages.
Written Opinion in PCT/CN2019/129636 dated Mar. 27, 2020, 5 pages.
First Office Action in Chinese Application No. 201811632931.8 dated Jun. 30, 2020, 15 pages.
First Office Action in Chinese Application No. 201910168616.2 dated Jul. 30, 2020, 16 pages.
First Office Action in Chinese Application No. 201910886148.2 dated Dec. 9, 2021, 21 pages.
Olaf Ronneberger et al., U-Net: Convolutional Networks for Biomedical image Segmentation, International Conference on Medical Image Computing and Computer-Assisted Intervention, 234-241, 2015.
Fausto Milletari et al., V-net: Fully convolutional neural networks for volumetric medical image segmentation, 2016 Fourth international Conference on 3D Vision, 565-571, 2016.
Zhang, Minging et al. , Multi-Task Convolutional Neural Network for Joint Bone Age Assessment and Ossification Center Detection from Hand Radiograph, Machine Learning in Medical Imaging, 681-689, 2019.
Zhou, Wenxiang, Automatic Evaluation of Bone Age Baed on X-ray Images, Chinese Master's Theses Full-text Database (Information Science and Technology), 2018, 83 pages.
He, Kaiming et al., Deep Residual Learning for image Recognition, 2016 IEEE Conference on Computer Vision and Pattern Recognition, 770-778, 2016.
Ren, Shaoqing at al. Faster R-CNN: Towards Real-Time Object Detection with Region Proposal Networks, IEEE Transactions on Pattern Analysis and Machine Intelligence, 2015, 14 pages.
Santiago Aja-Fernández et al., A Computational TW3 Classifier for Skeletal Maturity Assessment. A Computing with Words Approach, Journal of Biomedical Informatics, 37(2): 99-107, 2004.
Vladimir I. Iglovikov et al., Paediatric Bone Age Assessment Using Deep Convolutional Neural Networks, Deep Learning in Medical Image Analysis and Multimodal Learning for Clinical Decision Support, 360-308, 2018.
Sasan Mahmood et al., Skeletal Growth Estimation Using Radiographic Image Processing and Analysis, IEEE Transactions on Information Technology in Biomedicine, 4(4): 292-297, 2000.
Ren, Xuhua et al., Regression Convolutional Neural Network tor Automated Pediatric. Bone Age Assessment From Hand Radiograph, IEEE Journal of Biomedical and Health Informatics, 23(5): 2030-2038, 2018.
RSNA Pediatric Bone Age Challenge (2017).
Ramprasaath R. Selvaraju et al., Grad-CAM: Visual Explanations from Deep Networks via Gradient-Based Localization, 2017 IEEE International Conference on Computer Vision, 618-626, 2017.
C. Spampinato et al., Deep Learning for Automated Skeletal Bone Age Assessment in X-Ray Images, Medical Image Analysis, 36: 41-51, 2017.
Christian Szegedy et al., Rethinking the Inception Architecture for Computer Vision, 2016 IEEE Conference on Computer Vision and Pattern Recognition, 2818-2826, 2016.

* cited by examiner

500

500

SYSTEMS AND METHODS FOR OSSIFICATION CENTER DETECTION AND BONE AGE ASSESSMENT

CROSS-REFERENCE OF RELATED APPLICATIONS

This application is a Continuation of U.S. application Ser. No. 16/729,302, filed on Dec. 28, 2019, which claims priority of Chinese Patent Application No. 201811632931.8, filed on Dec. 29, 2018, Chinese Patent Application No. 201910168616.2, filed on Mar. 6, 2019, and Chinese Patent Application No. 201910886148.2, field on Sep. 19, 2019, the contents of each of which are hereby incorporated by reference.

TECHNICAL FIELD

The disclosure generally relates to an image processing technique, and more particularly relates to systems and methods for jointly detecting ossification centers and estimating a bone age based on a machine learning technique.

BACKGROUND

Skeletal bone age assessment is often performed in estimating the maturity of skeletal system in children, or in diagnosing growth disorders such as endocrine and metabolic abnormalities. Two main methods used in pediatric radiology are Greulich and Pyle (G&P) and Tanner-Whitehouse (TW2). The G&P method estimates the bone age by comparing the appearance of a patient's radiograph to the atlas of representative ages. The TW2 method focuses on 20 specific bones and assigns a staging score to each bone. In both cases, some manual assessment procedures, for example, the identification of ossification centers, a morphology of each ossification center, whether the epiphyseal line is closed, are time-consuming, and suffer from inter- and/or intra-observer variation. Bone age assessment depends on information of ossification centers. Thus, it is desirable to develop systems and methods for automated ossification center detection and automated bone age assessment based on results of the ossification center detection, which can facilitate to improve the diagnostic accuracy and/or efficiency.

SUMMARY

In a first aspect of the present disclosure, a method is provided. The method may include one or more operations. The one or more operations may be implemented on a computing device having at least one processor and at least one storage device. The at least one processor may obtain a bone age image of a subject. The at least one processor may generate a normalized bone age image by preprocessing the bone age image. The at least one processor may determine, based on the normalized bone age image, positions of a plurality of ossification centers using an ossification center localization (OCL) model.

In some embodiments, the at least one processor may estimate, based on the normalized bone age image and information related to the positions of the plurality of ossification centers, a bone age of the subject using a bone age assessment (BAA) model.

In some embodiments, the at least one processor may generate a report based on characteristic information of the subject, the positions of the plurality of ossification centers, or the bone age.

In some embodiments, the at least one processor may input the normalized bone age image and the information related to the positions of the plurality of ossification centers to a first part of the BAA model. The at least one processor may obtain gender information of the subject. The at least one processor may estimate the bone age of the subject by feeding outputs of the first part of the BAA model and the gender information to a second part of the BAA model.

In some embodiments, the OCL model and the BAA model may be jointly trained based on a plurality of training samples and a total loss function, wherein the total loss function is a linear combination of respective loss functions of the OCL model and the BAA model.

In some embodiments, the OCL model or the BAA model may include a fully convolutional neural network (FCN).

In some embodiments, the plurality of ossification centers may include a plurality of primary ossification centers and a plurality of secondary ossification centers. The OCL model includes a first OCL sub-model and a second OCL sub-model. The at least one processor may determine positions of the plurality of secondary ossification centers using the first OCL sub-model. The at least one processor may determine, based on the positions of the plurality of secondary ossification centers, positions of the plurality of primary ossification centers using the second OCL sub-model.

In some embodiments, the first OCL sub-model may output a first batch of probability maps each of which corresponds to the positions of the plurality of secondary ossification centers. The second OCL sub-model may output a second batch of probability maps each of which corresponds to the positions of the plurality of primary ossification centers.

In some embodiments, the at least one processor may generate, based on at least part of the positions of the plurality of secondary ossification centers, a region of interest (ROI) image from the normalized bone age image. The at least one processor may determine, based on the ROI image, the positions of the plurality of primary ossification centers using the second OCL sub-model.

In some embodiments, the at least one processor may designate one or more of the positions of the plurality of secondary ossification centers as positioning points. The at least one processor may generate the ROI image based on the positioning points.

In some embodiments, the at least one processor may generate a high-resolution image corresponding to the ROI image using an interpolation algorithm. The at least one processor may input the high-resolution image to the second OCL sub-model. The at least one processor may determine the positions of the plurality of primary ossification centers based on outputs of the second OCL sub-model.

In some embodiments, the first OCL sub-model or the second OCL sub-model may include a U-Net architecture.

In some embodiments, the bone age image may include a hand/wrist region of the subject. The at least one processor may segment the hand/wrist region from the bone age image. The at least one processor may adjust the hand/wrist region to a normalized position in the segmented bone age image. The at least one processor may resize the adjusted bone age image to a normalized image size. The at least one processor may transform the resized bone age image to a normalized gray-scale bone age image. The normalized gray-scale bone age image is designated as the normalized bone age image.

In a second aspect of the present disclosure, a system is provided. The system may include at least one storage device storing a set of instructions and at least one processor in communication with the at least one storage device. When executing the set of instructions, the at least one processor may direct the system to perform one or more operations as the following. The at least one processor may obtain a bone age image of a subject. The at least one processor may generate a normalized bone age image by preprocessing the bone age image. The at least one processor may determine, based on the normalized bone age image, positions of a plurality of ossification centers using an ossification center localization (OCL) model.

In some embodiments, the at least one processor may estimate, based on the normalized bone age image and information related to the positions of the plurality of ossification centers, a bone age of the subject using a bone age assessment (BAA) model.

In some embodiments, the at least one processor may generate a report based on characteristic information of the subject, the positions of the plurality of ossification centers, or the bone age.

In a third aspect, a non-transitory computer-readable medium is provided. The non-transitory computer-readable medium includes at least one set of instructions. When the at least one set of instructions are executed by at least one processor of a computer device, the at least one set of instructions directs the at least one processor to perform one or more operations as the following. The at least one processor may obtain a bone age image of a subject. The at least one processor may generate a normalized bone age image by preprocessing the bone age image. The at least one processor may determine, based on the normalized bone age image, positions of a plurality of ossification centers using an ossification center localization (OCL) model. The at least one processor may estimate, based on the normalized bone age image and information related to the positions of the plurality of ossification centers, a bone age of the subject using a bone age assessment (BAA) model.

In a fourth aspect of the present disclosure, a method is provided. The method may include one or more operations. The one or more operations may be implemented on a computing device having at least one processor and at least one storage device. The at least one processor may obtain a bone age image of a subject. The at least one processor may generate a normalized bone age image by preprocessing the bone age image. The at least one processor may perform, based on the normalized bone age image, a bone age assessment (BAA) and an ossification center detection (OCD) simultaneously using a multi-task network model.

In some embodiments, the multi-task network model may include a fully convolutional neural (FCN) network.

In some embodiments, the OCD may include a classification and a localization for a plurality of ossification centers. The multi-task network model may include a first subnet configured to classify the plurality of ossification centers, a second subnet configured to localize positions of the plurality of ossification centers, and a third subnet configured to assess a bone age of the subject.

In some embodiments, the multi-task network model may include a backbone network connected to at least one of the first subnet, the second subnet, and the third subnet.

In some embodiments, the first subnet, the second subnet, and the third subnet may share part of feature maps generated by the backbone network.

In some embodiments, the at least one processor may obtain one or more first feature maps generated by a contracting path of the backbone network. The at least one processor may classify the plurality of ossification centers by inputting the one or more first feature maps to the first subnet.

In some embodiments, the at least one processor may obtain one or more third feature maps generated by one or more stages of the expanding path of the backbone network. The one or more third feature maps may include the one or more first feature maps and the one or more second feature maps. The at least one processor may obtain gender information of the subject. The at least one processor may estimate the bone age of the subject by feeding the one or more third feature maps and the gender information to the third subnet.

In some embodiments, the multi-task network model may be trained based on a plurality of training samples and a total loss function. The total loss function is a linear combination of respective loss functions of the first subnet, the second subnet, and the third subnet.

In some embodiments, at least one of the loss functions of the first subnet, the second subnet, and the third subnet may include a focal loss function.

In a fifth aspect of the present disclosure, a system is provided. The system may include at least one storage device storing a set of instructions and at least one processor in communication with the at least one storage device. When executing the set of instructions, the at least one processor may direct the system to perform one or more operations as the following. The at least one processor may obtain a bone age image of a subject. The at least one processor may generate a normalized bone age image by preprocessing the bone age image. The at least one processor may perform, based on the normalized bone age image, a bone age assessment (BAA) and an ossification center detection (OCD) simultaneously using a multi-task network model.

In a sixth aspect of the present disclosure, a non-transitory computer-readable medium is provided. The non-transitory computer-readable medium includes at least one set of instructions. When the at least one set of instructions are executed by at least one processor of a computer device, the at least one set of instructions directs the at least one processor to perform one or more operations as the following. The at least one processor may obtain a bone age image of a subject. The at least one processor may generate a normalized bone age image by preprocessing the bone age image. The at least one processor may perform, based on the normalized bone age image, a bone age assessment (BAA) and an ossification center detection (OCD) simultaneously using a multi-task network model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
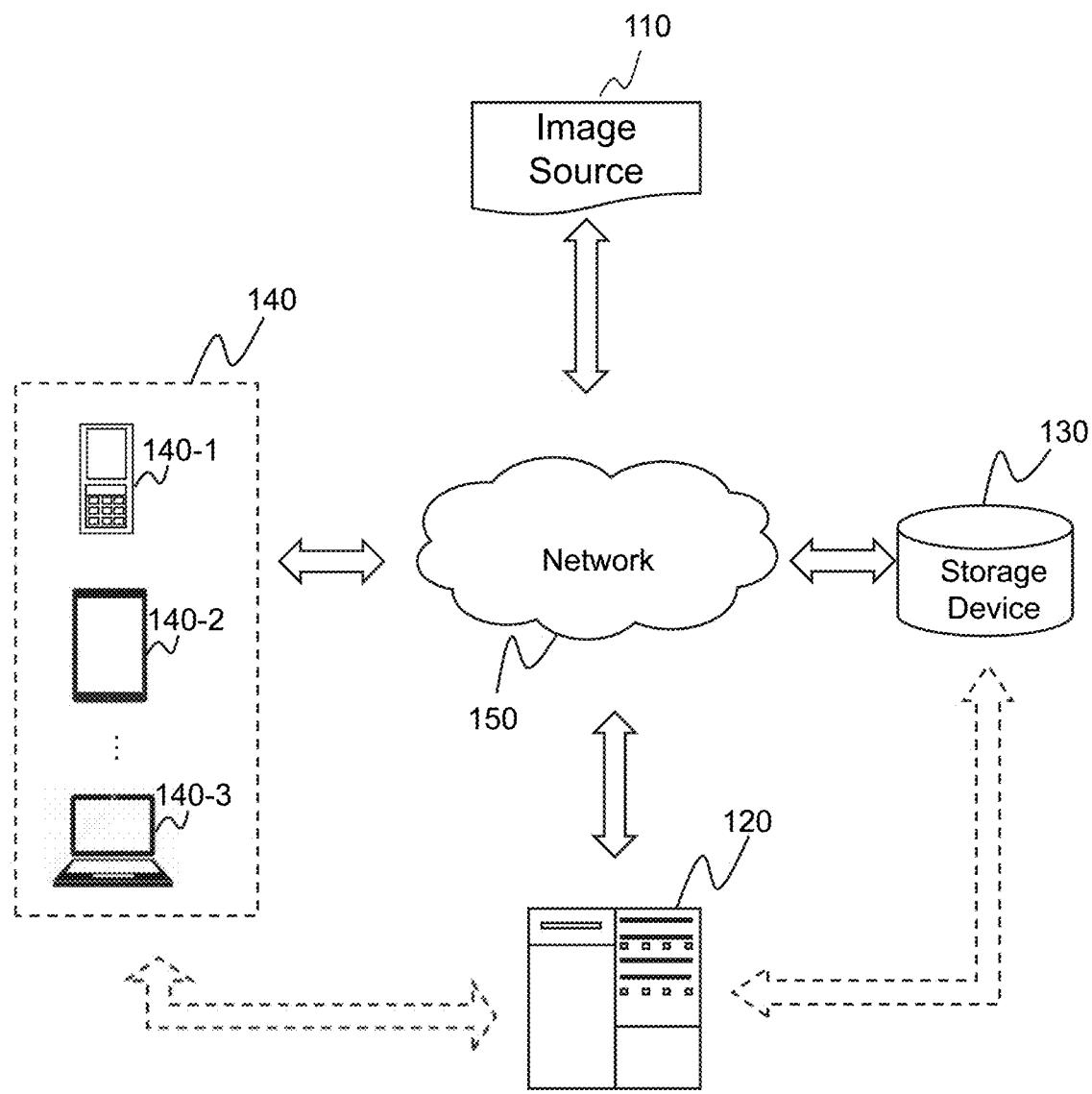
FIG. 1 is a schematic diagram illustrating an exemplary image processing system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

The systems and methods provided herein may be applied to assess human growth and development through joint bone age assessment (BAA) and ossification center detection (OCD) based on a bone age image (e.g., a hand radiograph). In some embodiments, the system may use an ossification center localization (OCL) model to localize ossification centers from the bone age image. For example, the OCL model may use a fully convolutional network (FCN) architecture, such as U-Net, V-Net, and so on. In some embodiments, the OCL model may include a first OCL sub-model and a second OCL sub-model. The first OCL sub-model may be responsible for localizing a plurality of secondary ossification centers. The second OCL sub-model may be responsible for localizing a plurality of primary ossification centers. The localization of the ossification centers can help a BAA related model to extract features from more meaning regions with the ossification centers related to the skeletal maturity. In some embodiments, the system may use a BAA model to estimate a bone age of a subject. The BAA model may use feature information related to the ossification centers to estimate the bone age. The BAA model may use an FCN architecture as well, such as Inception-V3 network. In some embodiments, the system may perform the OCD and the BAA simultaneously using a multi-task network model. The multi-task network model may include three task-specific subnets and a backbone network connected to the three task-specific subnets. The first subnet may be responsible for classifying the ossification centers from the bone age. The second subnet may be responsible for localizing the ossification centers. The third subnet may be responsible for estimating a bone age of the subject. The three task-specific subnets may share one or more feature maps extracted by convolutional layers in the backbone. Compared with an individual model for performing the ossification center classification, the ossification center localization or the bone age estimation, the multi-task network may have a high computing efficiency by sharing same feature maps. In some embodiments, the system may generate one or more reports based on results of the OCD and the BAA, such as BAA report and/or growth assessment (GA) report. Automated report generation may improve the diagnostic efficiency, accuracy, and/or reduce inter- and/or intra-observer variation.

Various embodiments of the systems and methods are described herein with reference to OCD, BAA, and/or GA based on carpal bones represented in hand radiographs for illustration purposes and not intended to be limiting. It is understood that the disclosed systems and methods are suitable to perform various applications including, e.g., OCD, BAA, and/or GA, based on bone age images of other regions of subjects.

FIG. 1 is a schematic diagram illustrating an exemplary image processing system according to some embodiments of the present disclosure. As shown in FIG. 1, imaging processing system 100 may include an image source 110, a processing device 120, a storage device 130, one or more terminal device(s) 140, and a network 150. The components in the image processing system 100 may be connected in one or more of various ways. Merely by way of example, the image source 110 may be connected to the processing device 120 directly (as indicated by the bi-directional arrow in dotted lines linking the image source 110 and the processing device 120) or through the network 150, as illustrated in FIG. 1. As another example, the storage device 130 may be connected to the processing device 120 directly (as indicated by the bi-directional arrow in dotted lines linking the storage device 130 and the processing device 120) or through the network 150, as illustrated in FIG. 1. As still a further example, the terminal device(s) 140 may be connected to the processing device 120 directly (as indicated by the bi-directional arrow in dotted lines linking the terminal device(s) 140 and the processing device 120) or through the network 150, as illustrated in FIG. 1.

The image source 110 may be configured to generate or provide image data related to a subject (e.g., a patient). In some embodiments, the image data may include at least one bone age image for ossification center detection and/or bone age assessment. In some embodiments, the image source 110 may include an imaging device (e.g., a scanner) configured to generate the image data related to the subject by scanning the subject. The imaging device may include a single-modality scanner (e.g., an X-ray scanner, an MRI scanner, a CT scanner, an ultrasonography scanner) and/or a multi-modality scanner (e.g., an X-ray-MRI scanner). For example, an X-ray scanner may be configured to generate an X-ray bone age image by scanning a hand/wrist region of the subject. In some embodiments, the image source 110 may include a database capable of providing the image data, such as an open source database for providing public dataset(s) (e.g., Radiological Society of North America (RSNA) public dataset) and/or a private database that provides private dataset(s) collected from medical organizations (e.g., local hospitals). In some embodiments, the database of the image source 110 may be integrated into the storage device 130. In some embodiments, the database of the image source 110 may be separated from the storage device 130. In some embodiments, the image data (e.g., bone age image(s)) may be transmitted to the processing device 120 to process, for example, detecting ossification centers and estimating a bone age from the bone age image(s) using one or more machine learning models. In some embodiments, the image data may be transmitted to a terminal device (e.g., the terminal device(s) 140) for display.

The processing device 120 may process data and/or information obtained from the image source 110, the storage device 130, the terminal device(s) 140, or other components of the image processing system 100. In some embodiments, the processing device 120 may apply a trained OCL model to localize ossification centers from a bone age image from the image source 110. In some embodiments, the processing device 120 may apply a trained BAA model to estimate a bone age of a subject based on outputs of the trained OCL model. In some embodiments, the processing device 120 may apply a trained multi-task network model to simultaneously estimate the bone age and detect ossification centers of different phalangeal, metacarpal and carpal bones. The multi-task network model may include at least two of a first subnet configured to localize positions of the ossification centers, a second subnet configured to classify the ossification centers, or a third subnet configured to estimate the bone age of the subject.

In some embodiments, by using a plurality of training samples, the OCL model, the BAA model and/or the multi-task network model may be trained by the processing device 120 or a specific processing device different from the processing device 120. For example, the specific processing device may be an external processing device separated from the image processing system 100. In some embodiments, one or more of these models (e.g., the OCL model, the BAA model and/or the multi-task network model) may be generated and/or updated by one processing device online or offline, while the applications of these models may be implemented on other processing device(s). For example, the processing device 120 may retrieve the OCL model, the BAA model, and/or the multi-task network model from a storage device and/or the other process device(s) and perform one or more tasks of the OCD and/or the BAA, such as the ossification center localization, the ossification center classification or the bone age assessment.

In some embodiments, the processing device 120 may include a single server or a server group. The server group may be centralized or distributed. In some embodiments, the processing device 120 may be local to or remote from the image processing system 100. For example, the processing device 120 may access information and/or data from the image source 110, the storage device 130, and/or the terminal device(s) 140 via the network 150. As another example, the processing device 120 may be directly connected to the image source 110, the one or more terminal devices 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

In some embodiments, the processing device 120 may include one or more processors (e.g., single-core processor(s) or multi-core processor(s)). Merely by way of example, the processing device 120 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 130 may store data, instructions, and/or any other information. In some embodiments, the storage device 130 may store data obtained from one or more components of the image processing system 100 (e.g., the image source 110, the processing device 120, and/or the one or more terminals 140). For example, the storage device 130 may store the OCL model, the BAA model, and/or the multi-task network model generated by the processing device 120 or other processing device. As another example, the storage device 130 may store a plurality of training samples for training the OCL model, the BAA model and/or the multi-task network model. As a further example, the storage device 130 may store algorithms and/or programs for generating the OCL model, the BAA model and/or the multi-task network model. In some embodiments, the storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the image processing system 100 (e.g., the image source 110, the processing device 120, and/or the terminal device(s) 140). One or more components in the image processing system 100 may access the data or instructions stored in the storage device 130 via the network 150. In some embodiments, the storage device 130 may be part of the processing device 120.

The one or more terminal devices 140 may be connected to and/or communicate with one or more components of the image processing system 100 (e.g., the image source 110, the processing device 120, and/or the storage device 130). For example, the one or more terminal devices 140 may send one or more instructions to the processing device 120 for implementing the OCD and/or the BAA. As another example, the one or more terminal devices 140 may display one or more results of the OCD and the BAA, such as positions of the ossification centers or an estimated bone age, and/or one or more reports related to one or more results of the OCD and the BAA (e.g., a BAA report and/or a GA report).

The one or more terminal devices 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc.

The network 150 may include any suitable network that can facilitate the exchange of information and/or data. In some embodiments, one or more components of the image processing system 100 (e.g., the image source 110, the processing device 120, the storage device 130, or the one or more terminal devices 140) may communicate with each other via the network 150. For example, the processing device 120 may obtain a bone age image from the image source 110 via the network 150. As another example, the processing device 120 may obtain a model (e.g., the OCL model, the BAA model and/or the multi-task network model) from the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the image processing system 100 may be connected to the network 150 to exchange data and/or information.

It should be noted that the above description of the image processing system 100 is merely provided for the purposes of illustration, and not intended to limit the scope of the present disclosure. For persons having ordinary skills in the art, multiple variations and modifications may be made under the teachings of the present disclosure. For example, the assembly and/or function of the image processing system 100 may be varied or changed according to specific implementation scenarios.

Figure 2:
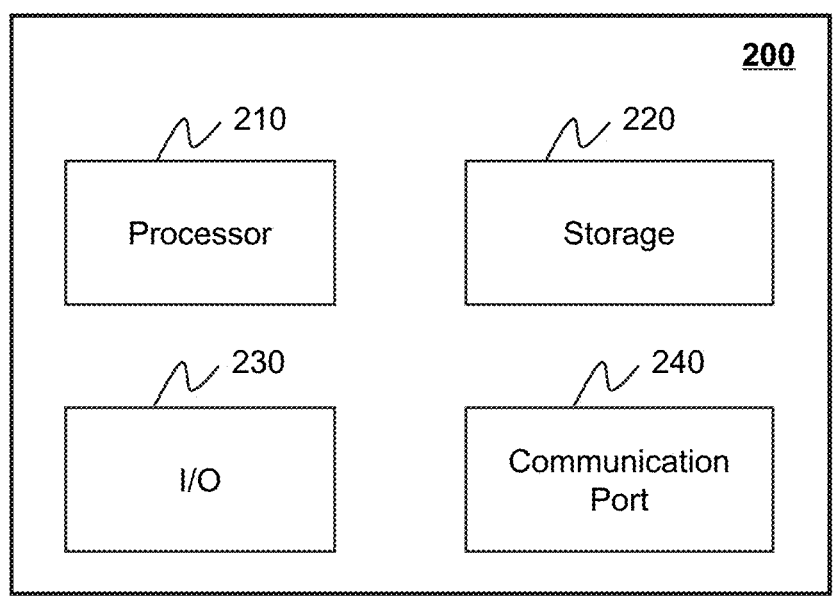
FIG. 2 is a schematic diagram illustrating hardware and/or software components of an exemplary computing device according to some embodiments of the present disclosure.

FIG. 2 is a schematic diagram illustrating hardware and/or software components of an exemplary computing device according to some embodiments of the present disclosure. As illustrated in FIG. 2, computing device 200 may include a processor 210, a storage 220, an input/output (I/O) 230, and a communication port 240. In some embodiments, the processing device 120 may be implemented on the computing device 200.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal device(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the image source 110, the terminal(s) 140, the storage device 130, or any other component of the image processing system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store one or more programs and/or instructions for directing the processing device 120 to implement one or more tasks of the OCD and the BAA. As another example, the storage 220 may store one or more programs and/or instructions for directing the processing device 120 to generate or invoke a machine learning model, such as an OCL model, a BAA model, or a multi-task network model.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the image source 110, the terminal device(s) 140, and/or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, 6G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
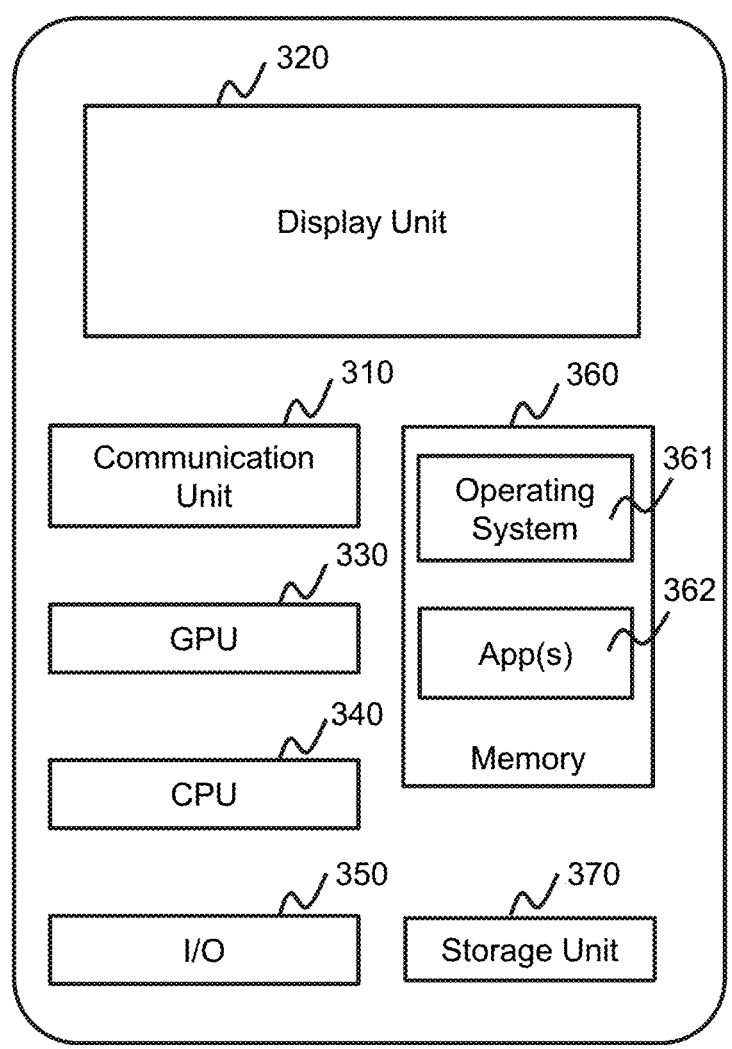
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device according to some embodiments of the present disclosure. In some embodiments, one or more components (e.g., a terminal device 140 and/or the processing device 120) of the image processing system 100 may be implemented on the mobile device 300 illustrated in FIG. 3

As illustrated in FIG. 3, the mobile device 300 may include a communication unit 310, a display unit 320, a graphics processing unit (GPU) 330, a central processing unit (CPU) 340, an I/O 350, a memory 360, and a storage unit 370. In some embodiments, any other suitable component, including but not limited to a system bus or a controller (not shown), may also be included in the mobile device 300. In some embodiments, a mobile operating system 361 (e.g., iOS, Android, Windows Phone, Harmony OS, etc.) and one or more applications 362 may be loaded into the memory 360 from the storage unit 370 in order to be executed by the CPU 340. The applications 362 may include a browser or any other suitable mobile apps for receiving and rendering information relating to image processing or other information from the processing device 120. User interactions with the information stream may be achieved via the I/O 350 and provided to the processing device 120 and/or other components of the image processing system 100 via the network 150.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
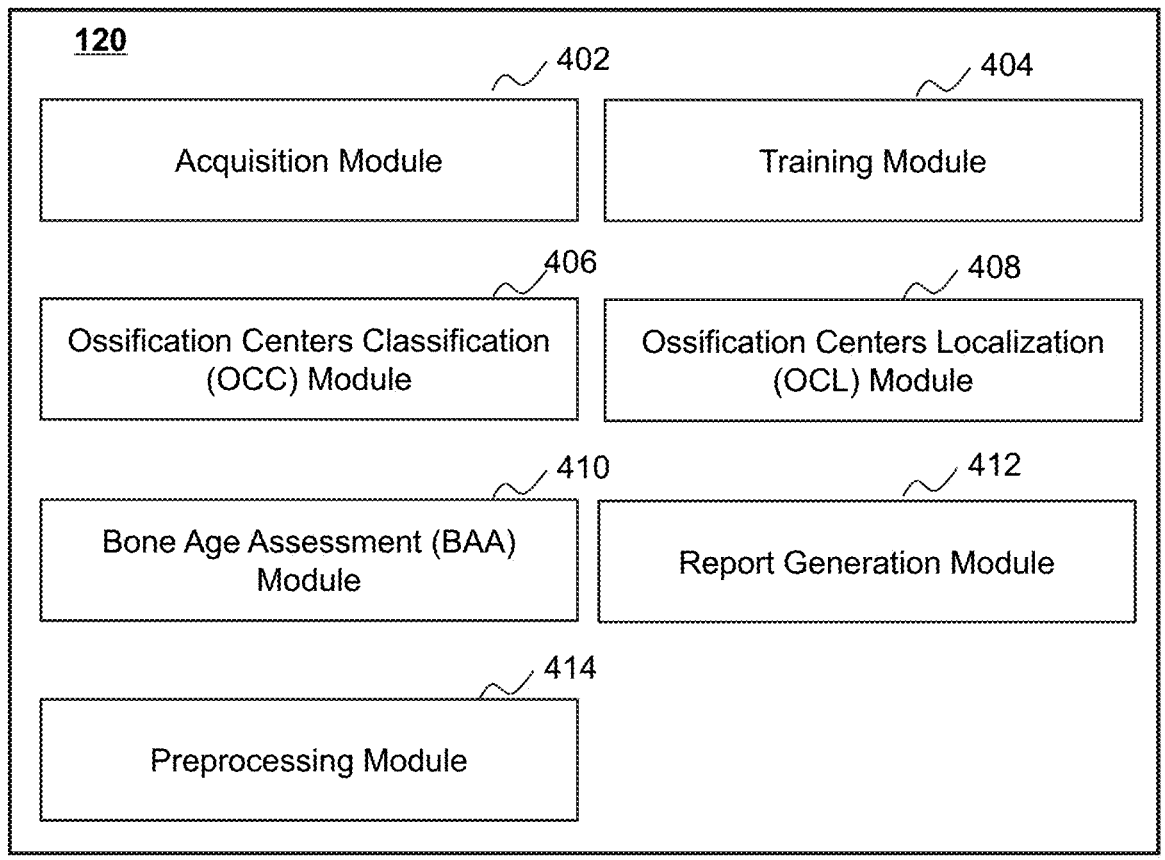
FIG. 4 is a block diagram illustrating an exemplary processing device according to some embodiments of the present disclosure.

FIG. 4 is a block diagram illustrating an exemplary processing device according to some embodiments of the present disclosure. In some embodiments, the processing device 120 may be implemented on a computing device 200 (e.g., the processor 210) illustrated in FIG. 2 or a CPU 340 as illustrated in FIG. 3. As illustrated in FIG. 4, the processing device 120 may include an acquisition module 402, a training module 404, an ossification center classification (OCC) module 406, an ossification center localization (OCL) module 408, a bone age assessment (BAA) module, a report generation module 412 and a preprocessing module 414. Each of the modules described above may be a hardware circuit that is designed to perform certain actions, e.g., according to a set of instructions stored in one or more storage media, and/or any combination of the hardware circuit and the one or more storage media.

The acquisition module 402 may be configured to obtain information related to the image processing system 100. For example, the acquisition module 402 may obtain a bone age image of a subject (e.g., a child). The bone age image may refer to an image including a specific bone region used for assessing a skeletal bone age of the subject. For example, the specific bone region may include a hand, a wrist, a knee, a clavicle, or the like, or any combination thereof. The bone age image may include an X-ray image, a CT image, an MRI image, an ultrasonography image, or the like. As used herein, the bone age image may be an X-ray image of a hand (also referred to as a hand radiograph). As another example, the acquisition module 402 may obtain a plurality of training samples from a storage device (e.g., the storage device 130).

The plurality of training samples may include hand radiographs for male subjects and/or female subjects. As a further example, the acquisition module 402 may obtain one or more trained models from a storage device (e.g., the storage device 130) or the training module 404. The one or more models may include an ossification center localization (OCL) model, a bone age assessment (BAA) model and/or a multi-task network model.

The training module 404 may be configured to determine one or more trained models of the image processing system 100. For example, the training module 404 may training an OCL model using the plurality of training samples. The trained OCL model may be configured to determine positions of a plurality of ossification centers (e.g., primary ossification centers and secondary ossification centers illustrated in FIG. 5A or FIG. 5B) from the bone age image. As another example, the training module 404 may jointly training an OCL model and a BAA model using the plurality training samples based on a total loss function. The total loss function may be a linear combination of a first loss function of the OCL model and a second loss function of the BAA model. The first loss function or the second loss function may be the same or different. For example, the first loss function may be a focal loss function and the second loss function may be a relative error function. The trained OCL model may be configured to determine positions of the plurality of ossification centers. The trained BAA model may be configured to estimate a bone age based on outputs of the trained OCL models. As a further example, the training module 404 may training the multi-task network model using the plurality of training samples. The multi-task network model may include three-specific subnets, that are, a first subnet, a second subnet and a third subnet. The first subnet may be configured to classify the plurality of ossification centers. The second subnet may be configured to localize the plurality of ossification centers. The third subnet may be configured to estimate a bone age of a subject. The training module 404 may jointly the first subnet, the second subnet and the third subnet based on a total loss function of respective loss functions. The total loss function may be a linear combination of the loss functions of the three subnets. The trained multi-task network model may be configured to classify the ossification centers. localize the ossification centers, and estimate the bone age simultaneously. More descriptions regarding the training of the OCL model, the BAA model and the multi-task network model may be found elsewhere in the present disclosure (e.g., FIG. 19 or FIG. 27, and the descriptions thereof).

The OCC module 406 may be configured to classify the plurality of ossification centers using the trained multi-task network model. For example, the OCC module 406 may invoke the multi-task network model to process the input bone age image, and obtain classification results output from the first subnet of the multi-task network model.

The OCL module 408 may be configured to localize the plurality of ossification centers. In some embodiments, the OCL module 408 may determine, based on a normalized bone age image, positions of the plurality of ossification centers using the OCL model. The normalized bone age image may be generated by the preprocessing module 414. In some embodiments, the OCL model may include a first OCL sub-model and a second OCL sub-model. The OCL module 408 may determine positions of the plurality of secondary ossification centers based on outputs of the first OCL sub-model. The OCL module 408 may generate, based on at least part of the positions of the plurality of secondary ossification centers, an ROI image from the normalized bone age image. The OCL module 408 may determine, based on the ROI image, positions of the plurality of primary ossification centers using the second OCL sub-model. In some embodiments, the OCL module 408 may determine positions of the ossification centers based on outputs of the second subnet of the multi-task network model. More descriptions regarding the ossification center localization may be found elsewhere in the present disclosure (e.g., FIG. 6, FIG. 8, FIG. 12, or FIG. 16 and the descriptions thereof).

The BAA module 410 may be configured to estimate a bone age of a subject based on the input bone age image. In some embodiments, the BAA module 410 may estimate, based on the normalized bone age image and information related to the positions of the plurality of ossification centers, the bone age of the subject using the BAA model. For example, the BAA module 410 may input the normalized bone age image and the information related to the positions of the plurality of ossification centers to a first part of the BAA model. The BAA module 410 may obtain gender information of the subject. The BAA module 410 may estimate the bone age of the subject by feeding outputs of the first part of the BAA model (e.g., the Inception-V3 network) and the gender information to a second part of the BAA model (e.g., one or more FC layers that is followed by the Inception-V3 network). In some embodiments, the BAA module 410 may estimate the bone age based on outputs of the third subnet of the multi-task network model. More descriptions regarding the ossification center localization may be found elsewhere in the present disclosure (e.g., FIG. 16 or FIG. 22, and the descriptions thereof).

The report generation module 412 may generate one or more reports based on characteristic information of the subject, the positions of the plurality of ossification centers or the bone age. In some embodiments, the one or more reports may include at least one of a BAA report or a growth assessment (GA) report for the subject. For example, the report generation module 412 may generate the BAA report or the GA report using a Natural Language Processing (NLP) technique. In some embodiments, the BAA report may include relevant results of the OCD and the BAA. For example, the BAA report may include the number of detected ossification centers and their respective position. In some embodiments, the GA report may provide information or suggestions for the growth and development of the subject. For example, the GA report may include a growth curve, a predicted height, growth assessment information, or the like, or any combination thereof. The automated report generation may facilitate to improve the diagnostic efficiency.

The preprocessing module 414 may be configured to generate the normalized bone age image by preprocessing the bone age image. In some embodiments, the preprocessing may include but not limited to segmenting a target region (e.g., the hand/wrist region), adjusting a position of the target region in the image, resizing the image size, and normalizing the grayscale base of the image. In the normalized bone age image, the target region may be located in a specific angle (e.g., an orthotopic position in the normalized bone age image). In some embodiments, the normalized bone age image may have a normalized image size (e.g., 512×512 pixels) and/or a normalized grayscale base. In some embodiments, the preprocessing module 414 may segment the hand/wrist region from the bone age image, for example, using a segmentation model. The preprocessing module 414 may adjust the hand/wrist region to a normalized position in the segmented bone age image. The preprocessing module 414 may resize the adjusted bone age image to a normalized image size. The preprocessing module 414 may transform the resized bone age image to a normalized grayscale bone age image. More descriptions regarding the preprocessing may be found elsewhere in the present disclosure (e.g., FIG. 6 or FIG. 9, and the descriptions thereof).

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the processing device 120 may not include the training module 404. The training module 404 may be set in other processing devices, such as a processing device separated from the image processing system 100.

Figure 5A:
FIGS. 5A and 5B are schematic diagrams illustrating an exemplary bone age image according to some embodiments of the present disclosure.
Figure 5B:

FIG. 5A and FIG. 5B are schematic diagrams illustrating an exemplary bone age image according to some embodiments of the present disclosure. The bone age image 500 may be an X-ray image of the left hand of a subject. As shown in FIG. 5A, there are a plurality of landmarks marked in the bone age image 500. The plurality of landmarks are numbered, such as landmarks 1-22. Each landmark may represent a specific ossification center to be recognized or analyzed. It is understood that an ossification center refers to a site where a bone begins to form in a specific bone or part of a bone as a result of an accumulation of osteoblasts in the connective tissue. In some embodiments, an ossification center may be categorized as a primary ossification center or a secondary ossification center. For example, the 22 ossification centers illustrated in FIG. 5A may include a plurality of primary ossification centers and a plurality of secondary ossification centers.

A primary ossification center may not form until a certain age, and the morphological characteristics of a primary ossification center can change over time. A plurality of primary ossification centers may be located in a carpal region of a hand. For children (e.g., 1-18 years old), the number (or count) and the shape of carpal bones may change over time. As shown in FIG. 5A, landmarks 12-20 represent primary ossification centers. Each landmark of landmarks 12-20 is marked on a geometric center of a corresponding primary ossification center. The landmarks 12-20 correspond to a capitate bone, a hamate bone, a triquetral bone, a lunate bone, a scaphoid bone, a trapezium bone, a trapezoid bone, an ulna bone, and a radius bone, respectively. The plurality of primary ossification centers may be composed of the 9 carpal bones mentioned above. In some embodiments, the plurality of primary ossification centers may be recognized by localizing the landmarks 12-20. The plurality of primary ossification centers may be used for estimating a bone age of a subject.

The plurality of secondary ossification centers may have formed in a central part of each developing bone during the prenatal development and exist at all ages. In some embodiments, the plurality of secondary ossification centers may be composed of metacarpal bones and phalanges. As shown in FIG. 5A, landmarks 1-11 and 21-22 represent secondary ossification centers. The landmarks 1-11 and 21-22 correspond to a distal phalange I, a proximal phalange I, a metacarpal bone I, a distal phalange III, a middle phalange III, a proximal phalange III, a metacarpal bone III, a distal phalange V, a middle phalange V, a proximal phalange V, a metacarpal bone V, an end of an ulna, and an end of a radius, respectively. Each landmark of landmarks 1-6 and 8-10 in FIG. 5A is marked above the corresponding ossification center. Each landmark of landmarks 7,11, 21 and 22 in FIG. 5A is marked below the corresponding ossification center. In some embodiments, the plurality of secondary ossification centers may be recognized by localizing the landmarks 1-11 and 21-22. In some embodiments, the two secondary ossification centers represented by landmarks 21 and 22, that is, end of the ulna and end of the radius, may be neglected without affect the bone age assessment. As show in FIG. 5B, landmarks 1-11 represented by the secondary ossification centers and landmarks 12-20 represented by the primary ossification centers can be marked. In some embodiments, the 11 secondary ossification centers represented by landmarks 1-11 may be recognized, while the two secondary ossification centers represented by landmarks 21-22 may be omitted in the bone age assessment.

Figure 6:
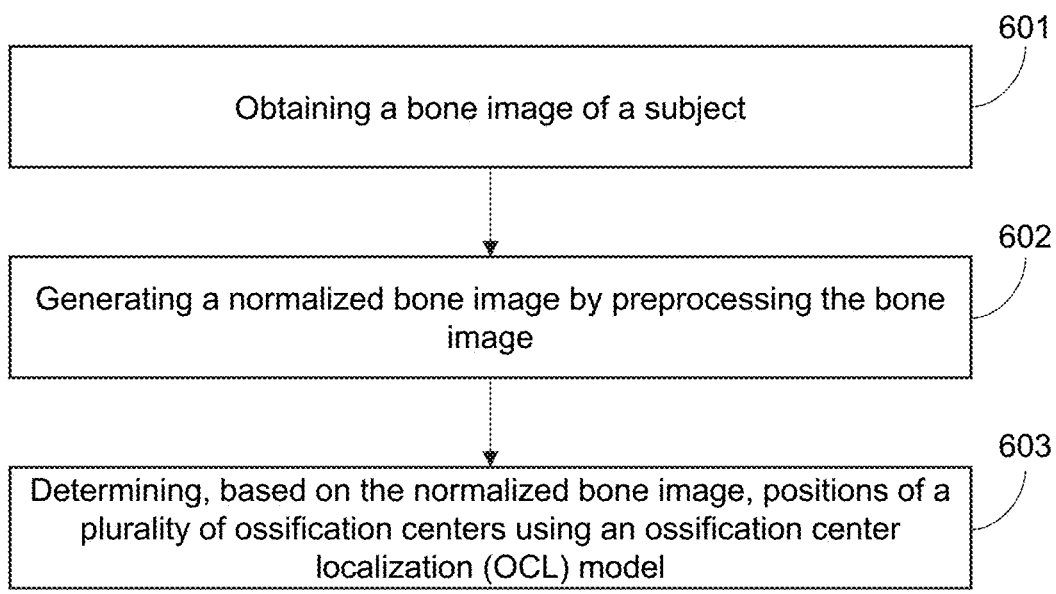
FIG. 6 is a flowchart illustrating an exemplary process for localizing ossification centers according to some embodiments of the present disclosure.

FIG. 6 is a flowchart illustrating an exemplary process for localizing ossification centers according to some embodiments of the present disclosure. In some embodiments, process 600 may be executed by the image processing system 100. For example, the process 600 may be implemented as a set of instructions (e.g., an application) stored in a storage device (e.g., the storage device 130, the storage 220, and/or the storage unit 370). In some embodiments, the processing device 120 (e.g., the processor 210 of the computing device 200, the CPU 340 of the mobile device 300, and/or one or more modules illustrated in FIG. 4) may execute the set of instructions to perform the process 600. The operations of the illustrated process presented below are intended to be illustrative. In some embodiments, the process 600 may be accomplished with one or more additional operations not described and/or without one or more of the operations discussed. Additionally, the order of the operations of the process 600 illustrated in FIG. 6 and described below is not intended to be limiting.

In 601, the processing device (e.g., the acquisition module 402 of the processing device 120) may obtain a bone age image of a subject (e.g., a patient).

In some embodiments, the bone age image may refer to an image including a specific bone region used for assessing a skeletal bone age of the subject. For example, the specific bone region may include a hand, a wrist, a knee, a clavicle, or the like, or any combination thereof. The bone age image may include an X-ray image, a CT image, an MRI image, an ultrasonography image, or the like. Merely for purposes of illustration, the bone age image may be an X-ray image of a hand (e.g., the bone age image 500 shown in FIG. 5A or FIG. 5B). As used herein, an X-ray image of a hand may also be referred to as a hand radiograph. In some embodiments, the hand radiograph may include a view of the hand and wrist region (referred as "hand/wrist region" for brevity) of the subject. In some embodiments, the hand radiograph may be a non-dominant hand radiograph. For example, for a left-handed person to be examined, a left-hand radiograph may be used for the OCD and/or the BAA. As another example, for a right-handed person to be examined, a right-hand radiograph may be used for the OCD and/or the BAA.

In some embodiments, the processing device 120 may obtain the bone age image (e.g., the hand radiograph) from the image source 110. For example, the image source 110 may include an imaging device, such as a scanner. The scanner (e.g., a CT scanner or an X-ray scanner) may generate the bone age image by scanning the hand/wrist region of the subject. The generated bone age image may be a left-hand radiograph or a right-hand radiograph. In some embodiments, the processing device 120 may obtain the bone age image from a storage device (e.g., the storage device 130 or a database of the image source 110).

In 602, the processing device (e.g., the preprocessing module 414 of the processing device 120) may generate a normalized bone age image by preprocessing the bone age image.

In some embodiments, the preprocessing may include segmenting a target region (e.g., the hand/wrist region), adjusting a position of the target region in the image, resizing the image size, and/or normalizing the grayscale base of the image. In the normalized bone age image, the target region may be located at a specific angle (e.g., an orthotopic position in the normalized bone age image). In some embodiments, the normalized bone age image may have a normalized image size (e.g., 512×512 pixels) and/or a normalized grayscale base.

In some cases, different bone age images may be generated under different imaging conditions or parameters (e.g., different X-ray intensities, image sizes, image backgrounds, etc.) Such bone age images may vary considerably in intensity, contrast, and grayscale base (e.g., white background and black bones or black background and white bone bones), which may cause a challenge for the ossification center detection. By performing the preprocessing, the target region (e.g., the hand/wrist region) may be extracted, extraneous objects in the bone age image (e.g., annotation marks on the bone age image) may be removed, the position of the target region in the bone age image may be adjusted, and/or the grayscale base of the bone age image may be normalized. In this way, the accuracy, efficiency, and/or robustness of the ossification center detection may be improved.

Merely for illustrative purposes, the bone age image to be recognized may be a hand radiograph including a hand/wrist region. The preprocessing module 414 may segment the hand/wrist region from the bone age image, for example, using a segmentation model. In some embodiments, the segmentation model may be used to perform a binary image segmentation for extracting a target region (i.e., the hand/wrist region). One or more extraneous objects (e.g., annotation marks) in the bone age image may be removed. For example, referring to FIG. 10, an annotation mark, "L," presented on the bone age image 910 can be removed through the binary segmentation. In some embodiments, the segmentation model may be a trained machine learning model. Exemplary segmentation models may include at least one of a convolutional neural network (CNN) model, a fully convolutional neural network (FCN) model, a generative adversarial network (GAN) model, a radial basis function (RBF) model, a deep belief nets (DBN) model, an Elman model, or the like, or a combination thereof. As used herein, the segmentation model may be an FCN model, such as a U-Net model illustrated in FIG. 10. It should be noted that various segmentation approaches may be used to extract the target region, and the descriptions herein are provided for illustration purposes and not intended to be limiting.

The preprocessing module 414 may adjust the hand/wrist region to a normalized position in the segmented bone age image. In some embodiments, the normalized position may be an orthotopic position in the segmented bone age image. In other words, the segmented hand/wrist region may be centered in the bone age image after the position adjustment. For example, the preprocessing module 414 may determine a rotation angle and/or a translation angle for the hand/wrist region using a principal component analysis (PCA) technique. Then the hand/wrist region may be rotated and/or translated to the normalized position according to the rotation angle and/or the translation angle. As another example, the preprocessing module 414 may determine an image barycenter of the bone age image, and adjust the hand/wrist region such that the barycenter of the hand/wrist region overlaps the image barycenter.

The preprocessing module 414 may resize the adjusted bone age image to a normalized image size. The normalized image size may be a specific image size, such as 1024×1024 pixels, 512×512 pixels.

Figure 9:
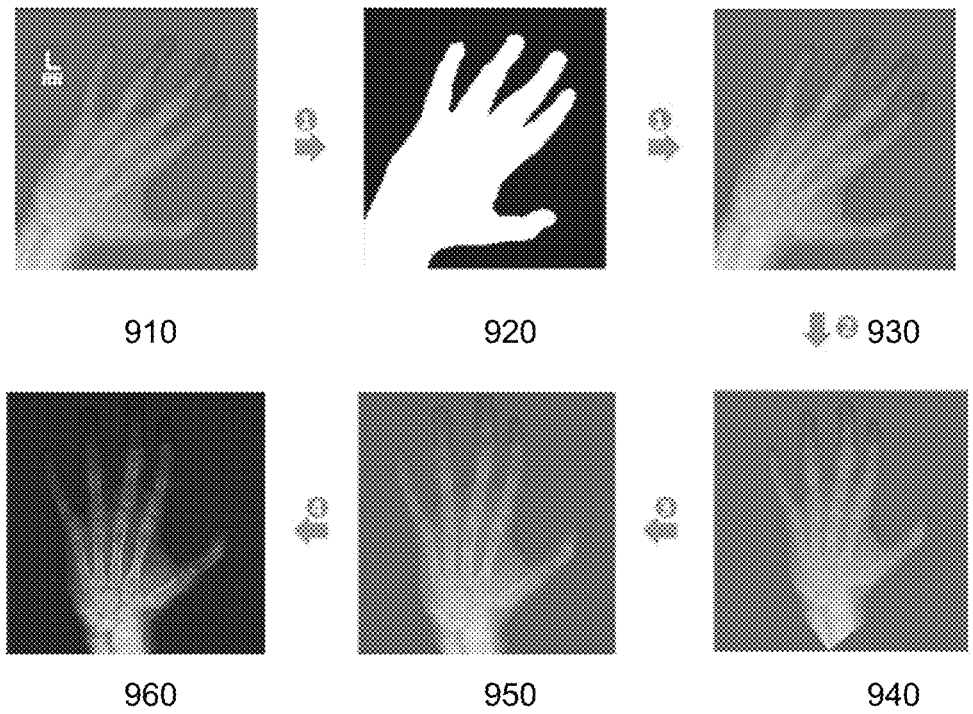
FIG. 9 is a schematic diagram illustrating a pipeline of a preprocessing procedure according to some embodiments of the present disclosure.

The preprocessing module 414 may transform the resized bone age image to a normalized grayscale bone age image (e.g., the bone age image 960 shown in FIG. 9). The normalized grayscale bone age image may be designated as a final normalized bone age image for the OCD or the BAA. In the final normalized grayscale bone age image, each pixel value may be normalized to fall in the range of (−1, 1). In some embodiments, the preprocessing module 414 may normalize the grayscale base through histogram equalization, whitening, denoising, sharpening, or the like. More descriptions regarding the preprocessing may be found elsewhere in the present disclosure (e.g., FIG. 9 and FIG. 10, and the descriptions thereof).

In 603, the processing device (e.g., the OCL module 408 of the processing device 120) may determine, based on the normalized bone age image, positions of a plurality of ossification centers using an OCL model. For example, the normalized bone age image may be taken as an input of the OCL model, then the OCL model may output a plurality of probability maps each of which corresponds to the position of one of the plurality of ossification centers. In some embodiments, a position (or coordinates) of an ossification center of the plurality of ossification centers may be derived from coordinates of the maximum response pixel in the probability map that corresponds to the ossification center.

As described in connection with FIG. 5A or FIG. 5B, the plurality of ossification centers may include the primary ossification centers (e.g., landmarks 1-13) and the secondary ossification centers (e.g., landmarks 14-22). The OCL model may include a first OCL sub-model and a second OCL sub-model. The first OCL sub-model may be used to localize the secondary ossification centers and the second OCL sub-model may be used to localize the primary ossification centers. For example, the OCL model may be a cascaded FCN model. The first OCL sub-model and the second OCL sub-model each may involve an individual FCN architecture. In some embodiments, the first OCL sub-model and the second OCL sub-model may be parallel or serial.

In some embodiments, the processing device 120 may input the normalized bone age image to the first OCL sub-model. The first OCL sub-model may output a first batch of probability maps. One of the first batch of probability maps may be indicative of a position of a secondary ossification center. In some embodiments, the position (or coordinates) of a secondary ossification center may be derived from coordinates of the maximum response pixel in a probability map of the first batch of probability maps.

The processing device 120 may generate a region of interest (ROI) image from the normalized bone age image based on at least part of the positions of the secondary ossification centers. The ROI image may include a carpal region where the primary ossification centers are located. In some embodiments, the ROI image may be input to the second OCL sub-model. The second OCL sub-model may output a first batch of probability maps. A second plurality of probability map may be indicative of a position of a primary ossification center. In some embodiments, the position (or coordinates) of a primary ossification center may be derived from coordinates of the maximum response pixel in a probability map of the second batch of probability maps. In this way, the second OCL sub-model just needs to retrieve data of the ROI image, instead of retrieving data of the entire bone age image, to localize the primary ossification centers. Thereby, the computation efficiency of the OCL model may be improved.

The primary ossification centers in the carpal region can be localized through the OCL model. For the children of different age groups, the number (or count) of appeared primary ossification centers may vary across the age groups. Compared with the localization of the secondary ossification centers, it may be more challenging to accurately localize the primary ossification centers. By using the cascade OCL model, the primary ossification centers and the secondary ossification centers may be separately localized, which may improve the accuracy, the efficiency and the robustness of the ossification center detection. More descriptions regarding the ossification center localization using the OCL model may be found elsewhere in the present disclosure (e.g., FIG. 7, FIG. 8, FIG. 14, and relevant descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the operation 602 may be omitted, that is, the preprocessing procedure may be omitted. As another example, the operation 602 may include one or more additional preprocessing operations, e.g., image enhancement, edge detection, hand mask generation, etc. Additionally, the order of the abovementioned preprocessing means in the operation 602 may be modified.

Figure 7:
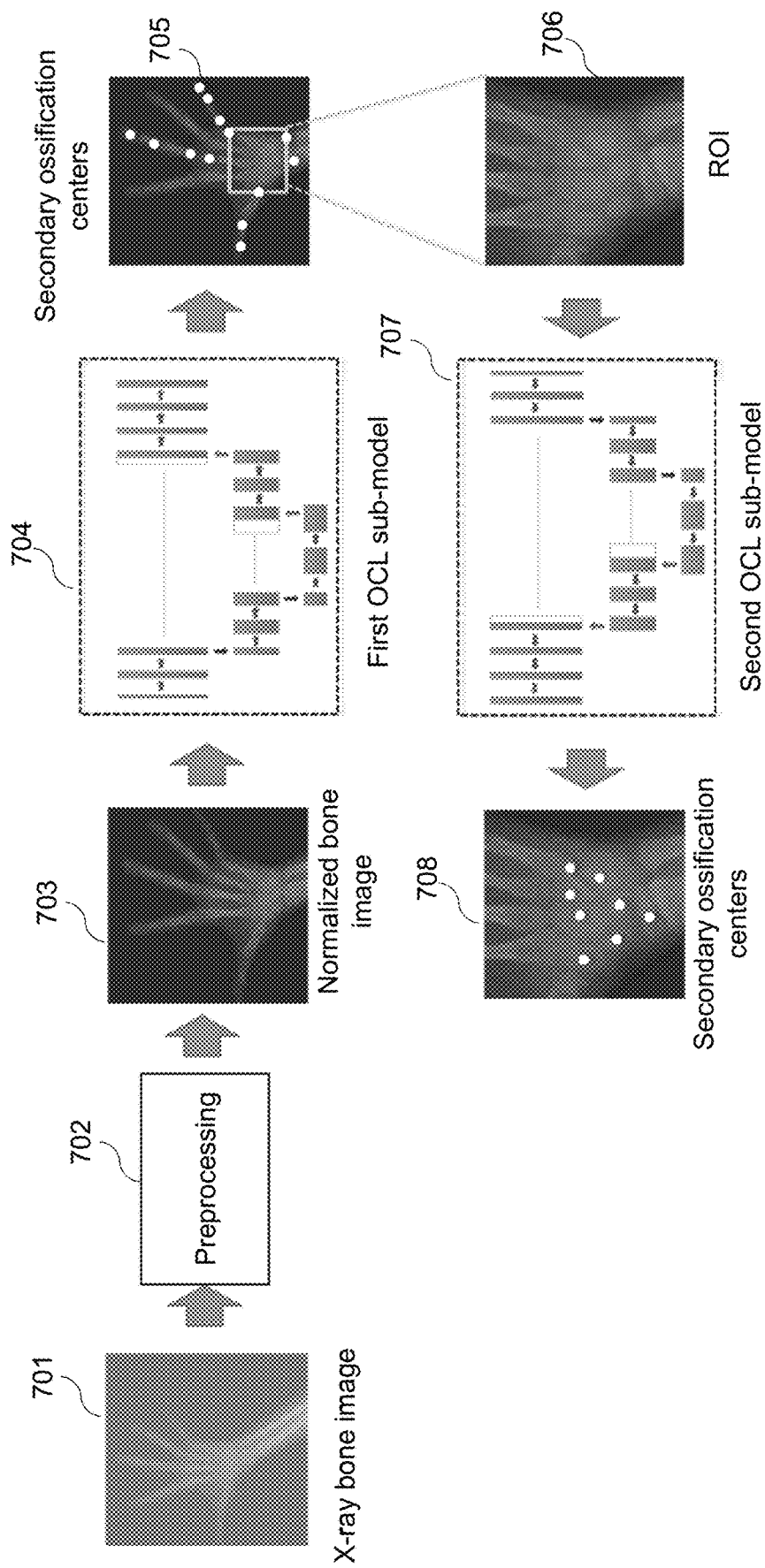
FIG. 7 illustrates a pipeline of ossification center localization using an OCL model according to some embodiments of the present disclosure.

FIG. 7 illustrates a pipeline of ossification center localization using an OCL model according to some embodiments of the present disclosure. The OCL model may be a cascade network model composed of a first OCL sub-model 704 and a second OCL sub-model 707. Before inputting to the first OCL sub-model 704, an X-ray bone age image 701 may be preprocessed through a preprocessing procedure 702. The X-ray bone age image 701 may be a hand radiograph. The hand radiograph may contain a hand/wrist region to be recognized. The preprocessing procedure 702 may include a segmentation (e.g., a binary segmentation) for extracting the hand/wrist region, adjusting a position of the hand/wrist region, resizing the image size, and/or normalizing a grayscale base of the image. More descriptions regarding the preprocessing procedure may be found elsewhere in the present disclosure (e.g., FIG. 9 and the descriptions thereof). After the preprocessing procedure 702, a normalized bone age image 703 may be generated. The normalized bone age image 703 may be fed to the first OCL sub-model 704 to localize the secondary ossification centers.

The first OCL sub-model 704 may be constructed based on an FCN model. The FCN model may include U-Net, V-Net, M-Net, a Visual Geometry Group (VGG) network, a residual neural network (ResNet), a dense neural network (DenseNet), or the like, or any combination thereof. Merely by way of example, the first OCL sub-model 704 uses a U-Net architecture, due to its ability to learn a network efficiently with a limited number of training samples. However, alternative networks mentioned above may be used in other embodiments. The U-Net architecture may include a top-down contracting path (left side) and a bottom-up expensive path (right side). In the contracting path, input feature maps may be down sampled to extract new feature maps as inputs to a next stage of the contracting path. In the expanding path, input feature maps may be up sampled to form new feature maps as inputs to a next stage of the expanding path. In some embodiments, the contracting path or the expanding path may include a plurality of convolutional layers for downsampling or upsampling. In some embodiments, at least one convolutional layer of the U-Net may be followed by a rectified linear unit (ReLU) and/or a max pooling operation. In some embodiments, at each downsampling step and/or upsampling step, a residual architecture may be embedded in order to accelerate the training of the U-Net. Descriptions regarding a U-Net architecture may be found in, for example, "U-Net: Convolutional Networks for Biomedical Image Segmentation" by Ronneberger et al., the contents of which are hereby incorporated by reference.

In some embodiments, the plurality of secondary ossification centers may be localized based on outputs of the first OCL sub-model 704. A visual localization result 705 presenting the secondary ossification centers is illustrated. Each landmark illustrated in 705 may represent a position of a secondary ossification center. According to at least part of the positions of the secondary ossification centers, an ROI image 706 may be generated. The ROI image 706 may contain a carpal region composed of the primary ossification centers.

The ROI image 706 may be fed to the second OCL sub-model 707. The second OCL sub-model 707 and the first OCL sub-model 704 may form an end-to-end network model. In some embodiments, similar to the first OCL sub-model 704, the second OCL sub-model 707 may be constructed based on an FCN model as well. For example, the second OCL sub-model 707 may use a U-Net architecture similar to the first OCL sub-model. In some embodiments, the primary ossification centers may be localized based on outputs of the second OCL sub-model 707. A visual localization result 708 presenting the primary ossification centers is illustrated. Each landmark illustrated in 708 may represent a position of a primary ossification center.

Figure 8:
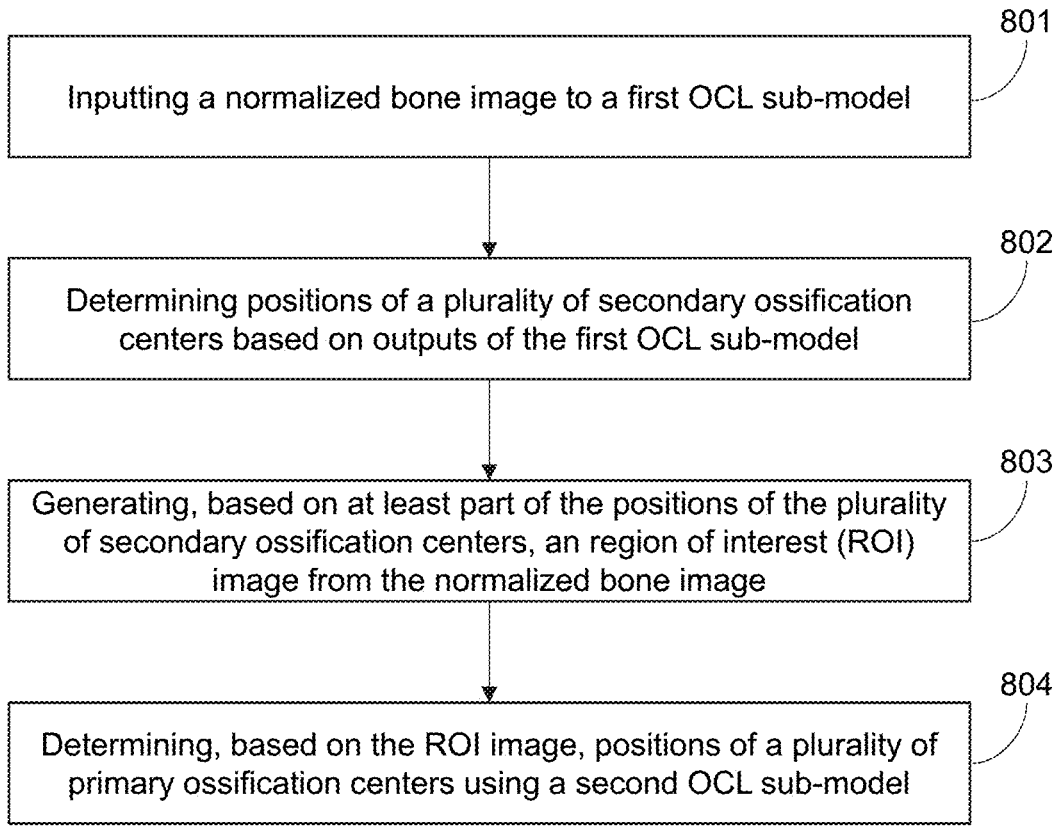
FIG. 8 is a flowchart illustrating an exemplary process for localizing ossification centers according to some embodiments of the present disclosure.

FIG. 8 is a flowchart illustrating an exemplary process for localizing ossification centers according to some embodiments of the present disclosure. In some embodiments, process 800 may be executed by the image processing system 100. For example, the process 800 may be implemented as a set of instructions (e.g., an application) stored in a storage device (e.g., the storage device 130, the storage 220, and/or the storage unit 370). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 800. In some embodiments, one or more operations of the process 800 may be performed to achieve at least part of operation 603 as described in connection with FIG. 6.

In 801, the processing device (e.g., the OCL module 408 of the processing device 120) may input a normalized bone age image to a first OCL sub-model (e.g., the first OCL sub-model 704). The normalized bone age image may be obtained by preprocessing a bone age image (e.g., a hand radiograph). The preprocessing procedure may be described in connection with FIG. 9.

Referring to FIG. 9, a pipeline of a preprocessing procedure according to some embodiments of the present disclosure is illustrated. The bone age image 910 may be segmented to extract a target region (e.g., the hand/wrist region). After the segmentation, a binary image 920 including the hand/wrist region is generated. As used herein, the binary image 920 (black background and white hand/wrist region) can be referred to as a first preprocessed bone age image. The annotation marks in the bone age image 910 (e.g., characters marked in the image) may be removed through the segmentation. In some embodiments, the binary image 920 may be designated as a hand mask. The mask may be used to remove extraneous artifacts from the bone age image 910 to generate a second preprocessed bone age image 930. Next, the segmented region (e.g., the hand/wrist region) may be adjusted to a specific position (e.g., the normalized position) in a new image. For example, the segmented hand/wrist region may be centered in a third preprocessed bone age image 940 to reduce or eliminate translational variance. Subsequently, the third preprocessed bone age image 940 may be resized to a normalized image size (e.g., 1024×1024 pixels, 512×512 pixels, etc.). A fourth preprocessed bone age image 950 may be generated by the resizing. Finally, the fourth preprocessed bone age image 950 may be transformed to a normalized grayscale bone age image through the histogram equalization, whitening, denoising and/or sharpening. The normalized grayscale bone age image may be deemed as a final preprocessed bone age image 960. The final preprocessed bone age image 960 may be used as input of the OCL model for the ossification center detection. By the preprocessing, the robustness and the adaptiveness of the OCL model may be improved, and a false positive rate of the output results may be reduced.

Figure 10:
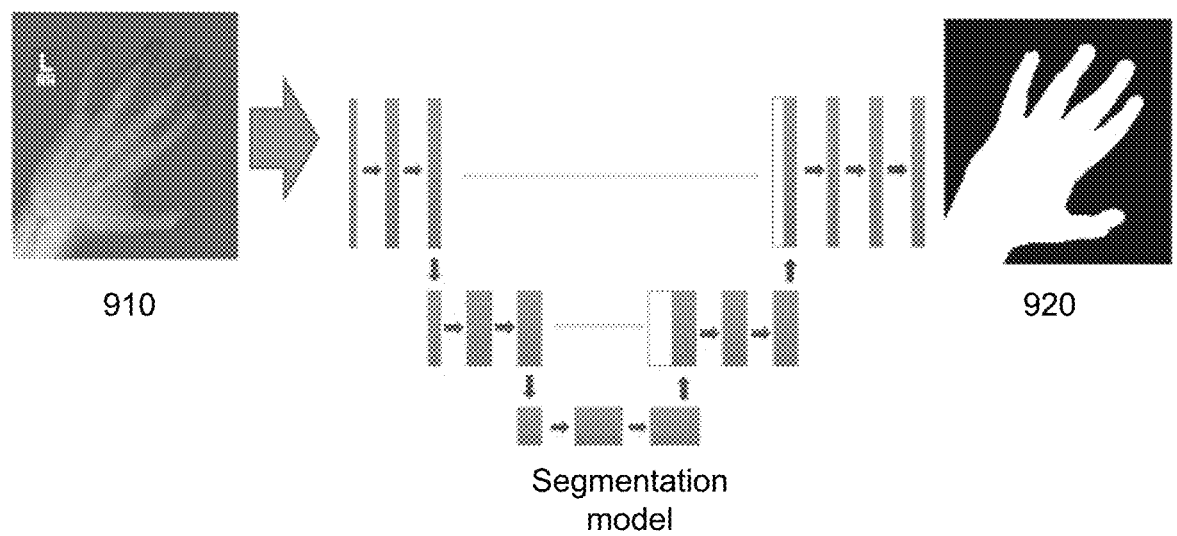
FIG. 10 is a schematic diagram illustrating a pipeline of a segmentation procedure according to some embodiments of the present disclosure.

In some embodiments, the bone age image 910 may be segmented to extract the hand/wrist region through a segmentation model. Referring to FIG. 10, a pipeline of a segmentation procedure according to some embodiments is illustrated. Through the segmentation model, the bone age image 910 may be segmented to extract the hand/wrist region. The segmentation model may output the segmented binary image 920. In some embodiments, the segmentation model may be a trained machine learning model. Exemplary segmentation models may include at least one of a convolutional neural network (CNN) model, a fully convolutional neural network (FCN) model, a generative adversarial network (GAN) model, a radial basis function (RBF) model, a deep belief nets (DBN) model, an Elman model, or the like, or a combination thereof. As used herein, the segmentation model may be an FCN model, such as a U-Net model. The U-Net architecture of the segmentation model may be same as or similar to that of the first OCL sub-model 704 or the second OCL sub-model 707 described in FIG. 7.

In 802, the processing device (e.g., the OCL module 408 of the processing device 120) may determine positions of a plurality of secondary ossification centers based on outputs of the first OCL sub-model.

Figure 11:
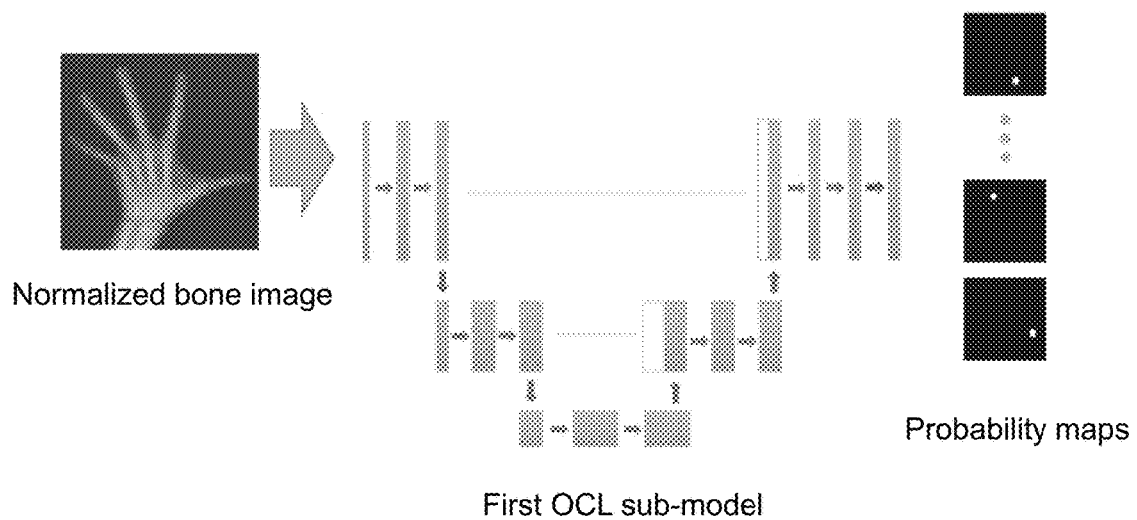
FIG. 11 is a schematic diagram illustrating a pipeline for localizing secondary ossification centers using a first OCL sub-model according to some embodiments of the present disclosure.

Referring to FIG. 11, a pipeline for localizing the secondary ossification centers using the first OCL sub-model is illustrated. The first OCL sub-model may use the U-Net architecture. The first OCL sub-model may take the normalized bone age image as an input. In some embodiments, the last convolutional layer of the first OCL sub-model may output a plurality of feature maps. In some embodiments, the plurality of feature maps may be transformed to a first batch of probability maps through a soft-max layer connected to the last convolutional layer. The first batch of probability maps are shown in FIG. 11. In each of the first batch of probability maps, a pixel value of a given pixel may represent a probability value that a specific second ossification center is centered at the pixel. The probability value may be in the range of [0, 1]. Merely for illustration, the first OCL sub-model may output the first batch of probability maps including S+1 probability maps, where S represents the number of the secondary ossification centers, such as S=13, or S=11. The S+1 probability maps may correspond to the S secondary ossification centers to be localized and the background of the normalized bone age image.

In some embodiments, the position (or coordinates) of a secondary ossification center may be derived from the coordinates of the maximum response pixel in a probability map of the first batch of probability maps. As used herein, the maximum response pixel in a probability map may refer to the pixel having the maximum probability value (or pixel value) in the probability map. In some embodiments, the processing device 120 may determine coordinates of the maximum response pixel of a probability map of the first batch of probability maps. The processing device 120 may designate the determined coordinates as the position of a secondary ossification center corresponding to the probability map. In some embodiments, the processing device 120 may compare each pixel value with a pixel threshold (e.g., 0.2, 0.3, 0.4, 0.5, 0.6, etc.) in a probability map. The pixel threshold may be in the range of [0,1]. If a value of a pixel is less than or equal to the pixel threshold, the pixel value may be reset as 0. If the value of the pixel is greater than the pixel threshold, the pixel value may be retained. In this way, the processing device 120 may generate a new probability map. The new probability map may be represented in the form of a binary image. The processing device 120 may perform a weighted average for all pixels and corresponding pixel values (i.e., probability values). The processing device 120 may determine the coordinates associated with a secondary ossification center based on the weighted averages. Given the probability map is a three-dimensional map, the processing device 120 may determine a coordinate of each dimension based on the Equation (1) as follows:

$$\begin{cases} \hat{x} = \frac{1}{N}\sum_{i=1}^{N} x_i \times P(x_i) \\ \hat{y} = \frac{1}{N}\sum_{i=1}^{N} y_i \times P(y_i), \\ \hat{z} = \frac{1}{N}\sum_{i=1}^{N} z_i \times P(z_i) \end{cases} \quad (1)$$

where $(\hat{x}, \hat{y}, \hat{z})$ represents the coordinates associated with the secondary ossification center to be localized, $(x_i, y_i, z_i)$ represents the coordinates of $i^{th}$ pixel in the probability map, $P(x_i)$, $P(y_i)$, $P(z_i)$ represents a respective probability value of each dimension, and N represents the number (or count) of the pixels of the probability map.

Figure 12:
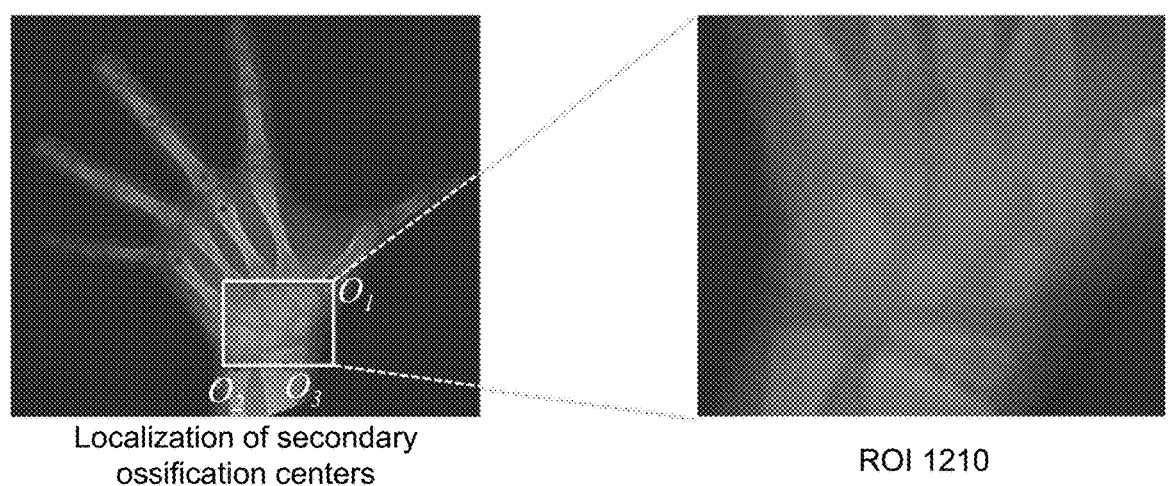
FIG. 12 is a schematic diagram illustrating an exemplary ROI image according to some embodiments of the present disclosure.

In 803, the processing device (e.g., the OCL module 408 of the processing device 120) may generate, based on at least part of the positions of the plurality of secondary ossification centers, an ROI image from the normalized bone age image. The ROI may include a carpal region covering the primary ossification centers. As illustrated in FIG. 12, positioning points $O_1$, $O_2$, and $O_3$ represent the positions of secondary ossification centers (landmarks) 3, 21, and 22, respectively, as illustrated in FIG. 5A. A bounding box covering the positioning points $O_1$, $O_2$, and $O_3$ may be constructed. The image region in the bounding box may be designated as the ROI image that includes the carpal region, such as ROI image 1210.

In 804, the processing device (e.g., the OCL module 408 of the processing device 120) may determine, based on the ROI image, positions of a plurality of primary ossification centers using a second OCL sub-model.

Figure 13:
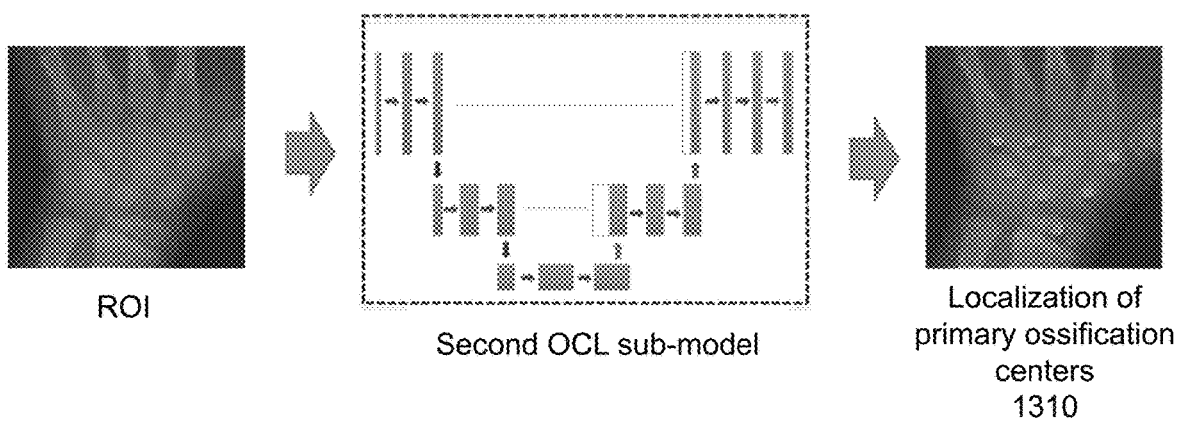
FIG. 13 is a schematic diagram illustrating a pipeline for localizing primary ossification centers using second OCL sub-model according to some embodiments of the present disclosure.

Referring to FIG. 13, a pipeline for localizing the primary ossification centers using the second OCL sub-model is illustrated. Similar to the first OCL sub-model, the second OCL sub-model may use the U-Net architecture as well. The ROI image related data may be fed to the second OCL sub-model. The second OCL sub-model may output a second batch of probability maps (not shown in FIG. 13). For example, the second OCL sub-model may output the second batch of probability maps including P+1 probability maps, where P represents the number (or count) of the primary ossification centers, such as P=9. The P+1 probability maps may correspond to the P primary ossification centers to be localized and the background of the ROI related image. The primary ossification centers may be localized based on the second batch of probability maps. The landmarks of the primary ossification centers may be presented, such as illustrated in 1310.

Similar to the localization of the secondary ossification centers mentioned above, the position (or coordinates) of a primary ossification center may be derived from the coordinates of the maximum response pixel in a probability map of the second batch of probability maps. For example, the processing device 120 may determine coordinates of the maximum response pixel of a probability map of the second batch of probability maps and designate the determined coordinates as the position of a primary ossification center corresponding to the probability map. As another example, the processing device 120 may determine the position of a primary ossification center according to Equation (1), which is not repeated herein.

In some embodiments, the first OCL sub-model and the second OCL sub-model may be trained online or offline using the same training samples, respectively. Each training sample may include a bone age image (e.g., a hand radiograph). In some embodiments, the bone age image may be a preprocessed bone age image that is preprocessed as described in connection with FIG. 9. For either the first OCL sub-model or the second OCL sub-model, respective parameters (e.g., the number (or count) of layers, the number (or count) of nodes, a weight value of a node, etc.) of the model may be iteratively updated until a termination condition is satisfied. Exemplary termination conditions may be that the value of a loss function obtained in a certain iteration is less than a threshold value, that a certain count of iterations have been performed, that the loss function converges such that the difference of the values of the loss function obtained in a certain number (or count) of consecutive iterations is within a threshold value, etc. Exemplary loss functions may include a focal loss function, a log loss function, a cross-entropy loss function, a Dice loss function, etc. In some embodiments, an adaptive moment estimation (Adam) optimizer (e.g., learning rate=0.0001) may be used to optimize the parameters of the OCL model.

Figure 14:
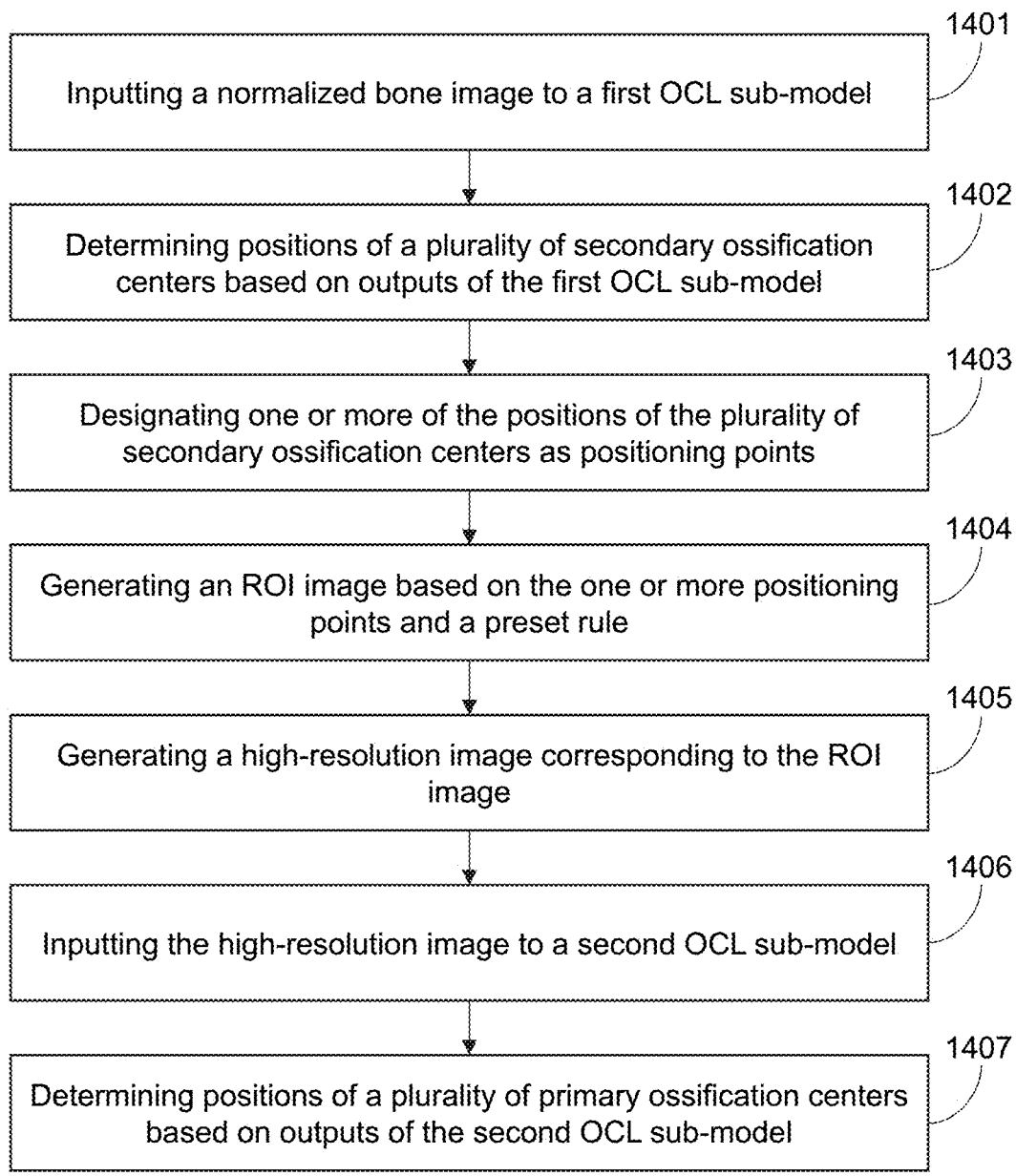
FIG. 14 is a flowchart illustrating an exemplary process for localizing ossification centers according to some embodiments of the present disclosure.

FIG. 14 is a flowchart illustrating an exemplary process for localizing ossification centers according to some embodiments of the present disclosure. In some embodiments, process 1400 may be executed by the image processing system 100. For example, the process 1400 may be implemented as a set of instructions (e.g., an application) stored in a storage device (e.g., the storage device 130, the storage 220, and/or the storage unit 370). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 1400. In some embodiments, one or more operations of the process 1400 may be performed to achieve at least part of operations as described in connection with FIG. 6 or FIG. 8.

In 1401, the processing device (e.g., the OCL module 408 of the processing device 120) may input a normalized bone age image to a first OCL sub-model (e.g., the first OCL sub-model 704). In some embodiments, the normalized bone age image may be generated by preprocessing a bone age image (e.g., a hand radiograph). In some embodiments, the preprocessing may include but not limited to segmenting a target region (e.g., the hand/wrist region), adjusting a position of the target region in the image, resizing the image size, and normalizing the grayscale base of the image. For example, the processing device 120 may perform the preprocessing as the preprocessing procedure described in FIG. 9. After the preprocessing procedure, the normalized bone age image (e.g., a normalized gray-scale bone age image) may be generated.

In 1402, the processing device (e.g., the OCL module 408 of the processing device 120) may determine positions of a plurality of secondary ossification centers based on outputs of the first OCL sub-model. As described in connection with FIG. 11, the first OCL sub-model may output a first batch of probability maps indicative of the positions of the secondary ossification centers. The position (or coordinates) of a secondary ossification center may be derived from the coordinates of the maximum response pixel in a probability map of the first batch of probability maps.

In 1403, the processing device (e.g., the OCL module 408 of the processing device 120) may designate one or more of the positions of the plurality of secondary ossification centers as positioning points. For example, as illustrated in FIG. 12, the secondary ossification centers (landmarks) 3, 12, and 13 may be selected as the positioning points $O_1$, $O_2$, and $O_3$.

In 1404, the processing device (e.g., the OCL module 408 of the processing device 120) may generate an ROI image based on the one or more positioning points and a preset rule. In some embodiments, the preset rule may define an aspect ratio, a shape, a size of the ROI image, a position relation between the one or more positioning points, or the like, or any combination thereof. In some embodiments, the ROI may include a carpal region covering the primary ossification centers.

Referring to FIG. 12, positioning points $O_1$, $O_2$, and $O_3$ represent the positions of secondary ossification centers (landmarks) 3, 21, and 22, respectively. A bounding box covering the positioning points $O_1$, $O_2$, and $O_3$ may be constructed in accordance with the preset rule. Merely by way of example, according to the preset rule, a right top vertex of the bounding box may be located at the positioning point $O_1$; the positioning point $O_2$ and the positioning point $O_3$ may be on the same side (e.g., the bottom side of the bounding box); the left bottom vertex of the bounding box may be to the left of the positioning point $O_2$; and a distance between the left bottom vertex and the positioning point $O_2$ may be set as a preset value (e.g., 50 pixels, 60 pixels, 70 pixels, etc.). In some embodiments, the size of the bounding box may be set as 500×600 pixels. The image region in the bounding box may be defined as the ROI image to be recognized, such as ROI image 1210.

Merely by way of example, the processing device 120 may obtain a probability map indicative of a position of metacarpal bone III (e.g., landmark 7 illustrated in FIG. 5A or FIG. 5B) based on the first OCL sub-model. The coordinates of landmark 7 may be determined based on the probability map. The landmark 7 may be designated as a positioning point. A bounding box of the ROI image may be constructed based on the positioning point and a preset rule.

In some embodiments, the preset rule may include a position relation between the positioning point and a side or a vertex of the bounding box, an area ratio of the bounding box and the normalized bone age image, and/or a size of the bounding box. For instance, the preset rule may define that the positioning point is located at the center of the top side of the bounding box, and the area ratio of the bounding box and the normalized bone age image is 0.5. The processing device 120 may construct the bounding box of the ROI image in accordance with the preset rule.

In some embodiments, the processing device 120 may obtain the probability maps indicative of positions of landmarks 21 and 22 illustrated in FIG. 5A. The coordinates of the landmarks 21 and 22 may be determined based on the probability maps. The landmarks 21 and 22 may be designed as the positioning points. A bounding box of the ROI image may be constructed based on the positioning points and a preset rule. For example, the preset rule defines that the two positioning points are located at the bottom side of the bounding box, a distance between the left side of the bounding box and the landmark 21 is 50 pixels, a distance between the right side of the bounding box and the landmark 22 is 100 pixels, and a preset aspect ratio of the bounding box. The processing device 120 may construct the bounding box of the ROI image in accordance with the preset rule.

Similarly, the processing device 120 may determine coordinates of metacarpal bone V (e.g., landmark 11 illustrated in FIG. 5A or FIG. 5B) and designate it as a positioning point. The processing device 120 may generate a bounding box of the ROI image based on the positioning point and a preset rule. For example, according to the preset rule, the landmark 11 is located at a left-top vertex of the bounding box, and a plurality of parameters (e.g., a height, a width, other vertexes' coordinates, etc.) related to the bounding box may be obtained. The processing device 120 may construct the bounding box based on the positioning point and the plurality of parameters. It should be noted that the relative position relation between the bounding box and the positioning point(s) described above are provided merely for illustration, and not intended to be limiting.

The processing device 120 may designate different positioning points to construct a bounding box indicative of the ROI image. For example, the position of metacarpal bone I (e.g., landmark 3) may be designated as a positioning point. As another example, the positions of proximal phalange I (e.g., landmark 2), the metacarpal bone V (e.g., landmark 11) and the end of an ulna (e.g., landmark 21) may be designated as the positioning points. As a further example, the positions of the metacarpal bone V (e.g., landmark 11), the end of an ulna 12 (e.g., landmark 21), and the end of a radius (e.g., landmark 22) may be designated as the positioning points. As still another example, the positions of metacarpal bone III (e.g., landmark 7), the end of an ulna (e.g., landmark 21), and the end of a radius (e.g., landmark 22) may be designated as the positioning points.

In 1405, the processing device (e.g., the OCL module 408 of the processing device 120) may generate a high-resolution image corresponding to the ROI image.

In some embodiments, the processing device 120 may generate the high-resolution image using an interpolation algorithm. Exemplary interpolation algorithms may include a nearest-neighbor interpolation algorithm, a bilinear interpolation algorithm, a trilinear interpolation algorithm, or the like. It should be noted that any suitable interpolation algorithm may be applied to generate the high-resolution image and not be intended to be limiting. It is understood that the image resolution can become relatively high after performing the interpolation.

Figure 15:
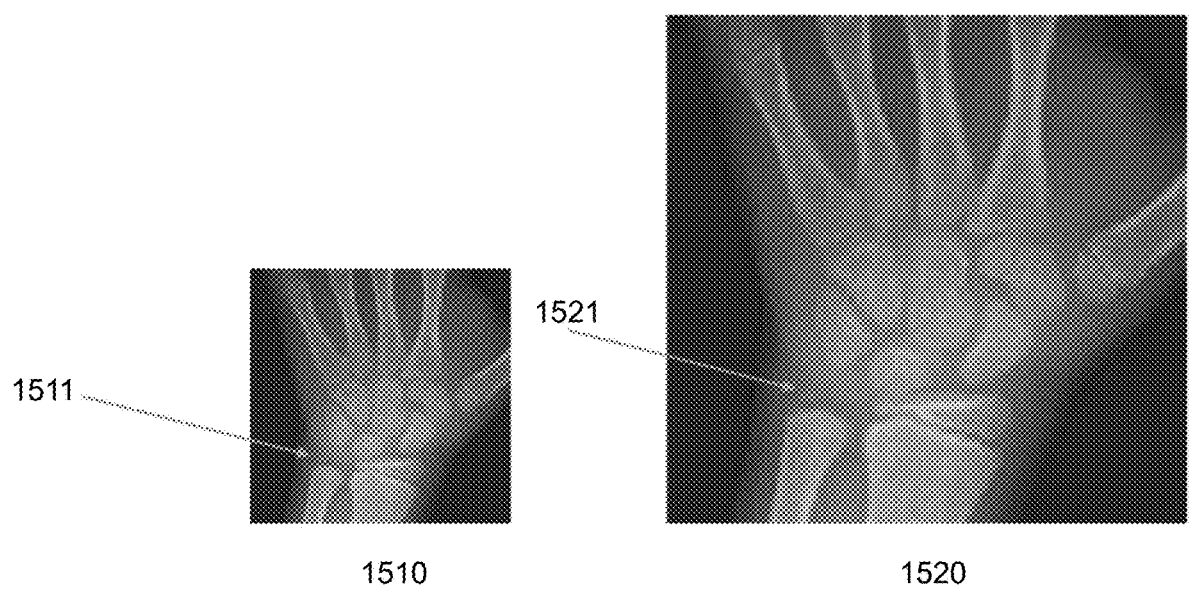
FIG. 15 illustrates an ROI image and a high-resolution image corresponding to the ROI image.

Referring to FIG. 15, an ROI image 1510 and a high-resolution image 1520 corresponding to the ROI image 1510 are illustrated. For example, the processing device 120 may perform the interpolation operation on the ROI image 1510 and generate a corresponding high-resolution image 1520. Given that the resolution of the ROI image 1510 is 256×256 pixels, while the resolution of the image can become 512×512 pixels after the interpolation. The high image resolution can depict more image details of the ROI (e.g., the carpal region 1521, corresponding to the carpal region 1511 in the ROI image 1510), which may improve the accuracy of localization of the primary ossification centers.

In 1406, the processing device (e.g., the OCL module 408 of the processing device 120) may input the high-resolution image to a second OCL sub-model (e.g., the second OCL sub-model 707).

In 1407, the processing device (e.g., the OCL module 408 of the processing device 120) may determine positions of a plurality of primary ossification centers based on outputs of the second OCL sub-model. As described in connection with FIG. 13, the high-resolution image may be taken an input of the second OCL sub-model. The second OCL sub-model may output a second batch of probability maps indicative of the positions of the primary ossification centers. The position (or coordinates) of a primary ossification center may be derived from the coordinates of the maximum response pixel in a probability map of the second batch of probability maps.

In general, a non-dominant hand of the subject can be imaged to provide a bone age image to be recognized or analyzed. For example, for a right-handed person, a left-hand radiograph may be used for ossification center detection and/or bone age assessment. As another example, for a left-handed person, a right-hand radiograph may be used for ossification center detection and/or bone age assessment. In some embodiments, the OCL model may be specialized to determine positions of the ossification centers based on the left-hand radiograph. In some embodiments, the OCL model may be specialized to determine positions of the ossification centers based on the right-hand radiograph. In some embodiments, the OCL model may be adaptive to determine positions of the ossification centers based on either the left-hand radiograph or the right-hand radiograph.

In some embodiments, for the OCL model specialized for using the left-hand radiograph, the processing device 120 may determine whether the hand/wrist represented in the bone age image is the left hand/wrist before performing the operation 1403. In some embodiments, when the hand/wrist is identified as the right hand/wrist, the right hand/wrist region can be flipped such that the right hand/wrist region is presented in the form of the left hand/wrist. In some embodiment, when the hand/wrist is identified as the left hand/wrist, the operation 1403 may proceed. In some embodiments, the processing device 120 may determine whether the hand/wrist in the normalized bone age image is the left hand/wrist based on positions of one or more secondary ossification centers.

For example, the processing device 120 may obtain positions of the metacarpal bone I (e.g., landmark 3) and the metacarpal bone V (e.g., landmark 11). The processing device 120 may determine whether the position of the landmark 3 is at the right of the position of the landmark 11. For the left hand, the landmark 3 is located at a proximal joint of the thumb, the landmark 11 is located at a proximal joint of the little (or baby) finger. The proximal joint of the thumb is to the right of the proximal joint of the little finger. If the judgment result shows that the landmark 3 is to the right of the landmark 11, the hand/wrist in the normalized bone age image may be identified as the left hand/wrist. Otherwise, the hand/wrist in the normalized bone age image may be identified as the right hand/wrist.

As another example, the processing device 120 may obtain positions of the proximal phalange I (e.g., landmark 2), the metacarpal bone I (e.g., landmark 3), the distal phalange V (e.g., landmark 8), the middle phalange V (e.g., landmark 9), the proximal phalange V (e.g., landmark 10), and the metacarpal bone V (e.g., landmark 11). The processing device 120 may identify the thumb and the little finger based on the number (or count) of the identified secondary ossification centers. The processing device 120 may further determine whether the hand/wrist to be recognized is the left hand based on the position relation between the thumb and the little finger. In some embodiments, the processing device 120 may identify the secondary ossification centers on a leftmost finger in the hand radiograph, and determine whether the leftmost finger is the little finger or the thumb based on the number (or count) of the secondary ossification centers on the leftmost finger. For example, when the number (or count) of the secondary ossification centers on the leftmost finger is 4, the leftmost finger may be identified as the little finger. Based on the determination that the little finger of the left hand is on the far left, the processing device 120 may identify that the hand/wrist to be recognized is the left hand/wrist. Otherwise, the hand/wrist may be identified as the right hand/wrist. Similarly, the processing device 120 may also determine whether the hand/wrist to be recognized is the left hand by identifying the secondary ossification centers on a rightmost finger.

As a further example, the processing device 120 may obtain the position of the metacarpal bone I (e.g., landmark 3), and identify the thumb based on the position of the landmark 3. The processing device 120 may further identify whether the hand/wrist to be recognized is the left hand based on the location of the thumb. For example, when the landmark 3 is at the right of the normalized bone age image, the thumb may be at the right of the normalized bone age image as well. Thus, the hand/wrist may be recognized as the left hand. Otherwise, the hand/wrist may be recognized as the right hand.

It should be noted that the abovementioned identification regarding the left hand or the right hand are merely provided for illustration, and not intended to limit the scope of the present disclosure. For example, the processing device 120 may identify the metacarpal bone V (e.g., landmark 11) and identify the left hand or the right hand based on the position of the landmark 11. As another example, the processing device 120 may identify the landmark 11, the landmark 21, and the landmark 22. The left hand or the right hand may be determined based on the positions of the landmark 11, the landmark 21, and the landmark 22. As a further example, the processing device 120 may identify the landmark 2, the landmark 21, and the landmark 22. The left hand or the right hand may be determined based on the landmark 2, the landmark 21, and the landmark 22.

In some embodiments, for the OCL model configured to us a right-hand radiograph as input, the processing device 120 may determine whether the hand/wrist in the normalized bone age image is a right hand/wrist before performing the operation 1403. The identification of the right hand/wrist may be performed similar to the identification of the left hand/wrist mentioned above, and is not repeated herein. In some embodiments, when the hand/wrist is identified as the left hand/wrist, the left hand/wrist region can be flipped such that the left hand/wrist region is presented in the form of the right hand/wrist. In some embodiment, when the hand/wrist is identified as the right hand/wrist, the operation 1403 may be performed.

In some embodiments, for an OCL model adaptive to use either a right-hand radiograph or a left-hand radiograph as input, the processing device 120 may input a hand radiograph of either side to the OCL model, and determine positions of the ossification centers based on outputs of the OCL model. Such an adaptive OCL model may be trained based on the training samples composed of right-hand radiographs and/or left-hand radiographs. In some embodiments, when all of the training samples are radiographs of a same side, some radiographs may be flipped at a random rate so that the training data may include feature data of both the left hand/wrist and the right hand/wrist. For instance, 30%, 40%, 50%, or 60% of the training samples are flipped to provide radiographs of a different side than the remaining radiographs. These training data may be used to train an OCL model adaptive to use either a right-hand radiograph or a left-hand radiograph as input. The ratio of training samples of one side to the other side may be adjusted according to different goals.

Figure 16:
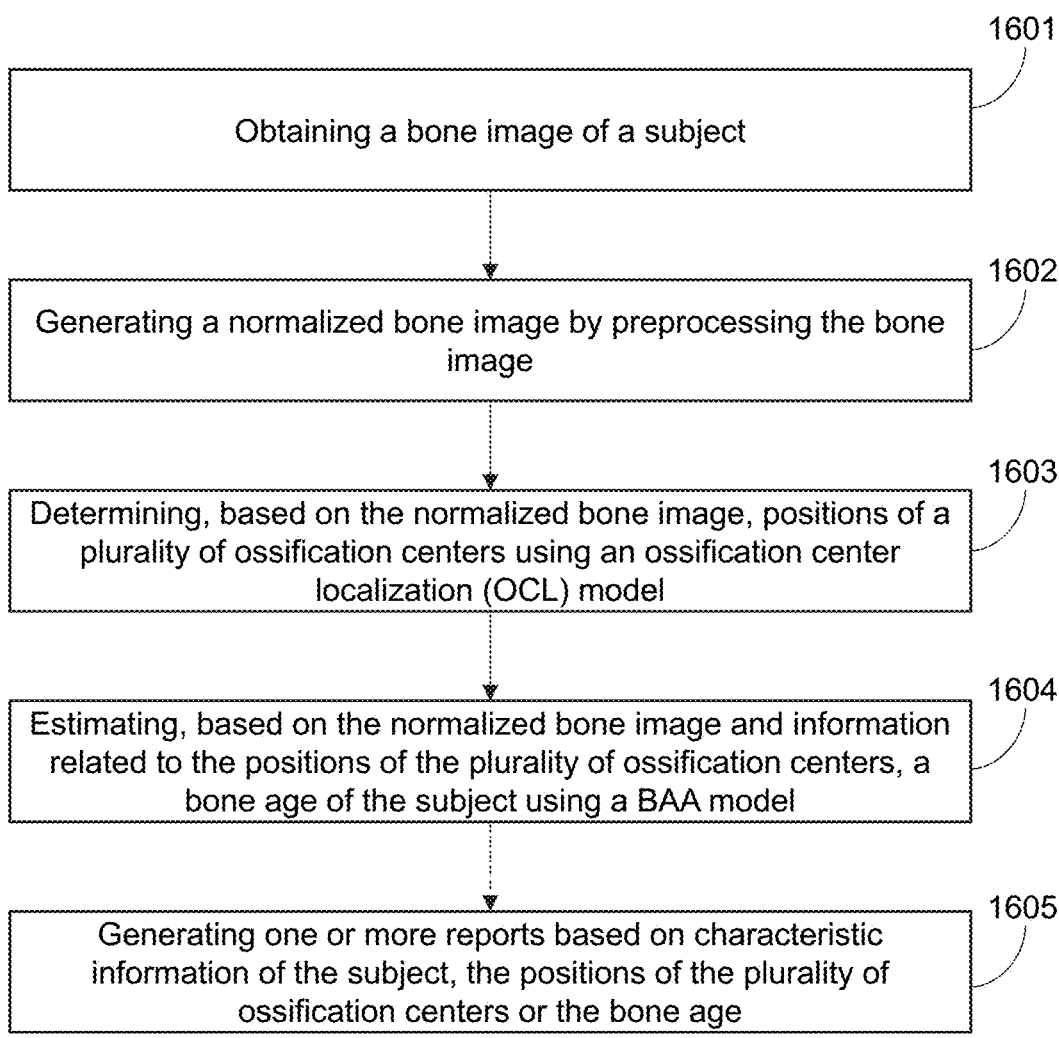
FIG. 16 is a flowchart illustrating an exemplary process for ossification center detection (OCD) and bone age assessment (BAA) according to some embodiments of the present disclosure.

FIG. 16 is a flowchart illustrating an exemplary process for ossification center detection (OCD) and bone age assessment (BAA) according to some embodiments of the present disclosure. In some embodiments, process 1600 may be executed by the image processing system 100. For example, the process 1600 may be implemented as a set of instructions (e.g., an application) stored in a storage device (e.g., the storage device 130, the storage 220, and/or the storage unit 370). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 1600. The operations of the illustrated process presented below are intended to be illustrative. In some embodiments, the process 1600 may be accomplished with one or more additional operations not described and/or without one or more of the operations discussed. Additionally, the order of the operations of the process 1600 illustrated in FIG. 16 and described below is not intended to be limiting.

In 1601, the processing device (e.g., the acquisition module 402 of the processing device 120) may obtain a bone age image (e.g., a hand radiograph) of a subject (e.g., a child). The bone age image may be used for the OCD and/or the BAA. The descriptions regarding the bone age image may be found elsewhere in the present disclosure and not be repeated herein. See, e.g., operation 601 in FIG. 6.

In 1602, the processing device (e.g., the OCL module 408 of the processing device 120) may generate a normalized bone age image by preprocessing the bone age image. In some embodiments, the preprocessing may include but not limited to segmenting a target region (e.g., the hand/wrist region), adjusting a position of the target region in the image, resizing the image size, and normalizing the gray-scale base of the image. For example, the processing device 120 may perform the preprocessing as the preprocessing procedure described in FIG. 9. After the preprocessing procedure, the normalized bone age image (e.g., a normalized gray-scale bone age image) may be generated. The normalized bone age image may be input to the OCL model and/or the BAA model for the OCD and the BAA. By the preprocessing, the target region (e.g., the hand/wrist region) may be extracted, all extraneous objects on the bone age image (e.g., annotation marks on the bone age image) may be removed, the position of the target region on the bone age image may be normalized, and the grayscale base of the bone age image may be normalized. A false positive rate of the OCL model may be reduced, thereby the detection accuracy may be improved.

In 1603, the processing device (e.g., the OCL module 408 of the processing device 120) may determine, based on the normalized bone age image, positions of a plurality of ossification centers using an ossification center localization (OCL) model.

As described in connection with FIG. 5A or FIG. 5B, the plurality of ossification centers may include the primary ossification centers and the secondary ossification centers. In some embodiments, the ossification centers to be recognized may include 22 ossification centers illustrated in FIG. 5A. In some embodiments, the ossification centers to be recognized may be include 20 ossification centers illustrated in FIG. 5B. The two ossification centers marked by landmarks 12 and 13 may be neglected and not be detected. In some embodiments, the OCL model may be adopted to localize the plurality of ossification centers.

The OCL model may be a trained machine learning model. Exemplary machine learning models may include a convolutional neural network (CNN) model, a fully convolutional neural network (FCN) model, a generative adversarial network (GAN) model, a radial basis function (RBF) model, a deep belief nets (DBN) model, an Elman model, or the like, or a combination thereof. In some embodiments, the OCL model may be constructed based on an FCN model. Exemplary FCN models may include U-Net, V-Net, M-Net, a Visual Geometry Group (VGG) network, a residual neural network (ResNet), a dense neural network (DenseNet), or the like, or any combination thereof.

In some embodiments, the OCL model may use a U-Net architecture. Referring to FIG. 7, the OCL model may be a cascade network model composed of the first OCL sub-model 704 and the second OCL sub-model 707. The normalized bone age image may be fed to the first OCL sub-model 704, then the first OCL sub-model 704 may output a plurality of probability maps for localizing the secondary ossification centers. For example, the plurality of probability maps may include 11 probability maps associated with the eleven secondary ossification centers (e.g., landmarks 1-11) to be localized, and one probability map associated with the background of the input normalized bone age image. Each of the 11 probability maps may correspond to a position of one of the 11 secondary ossification centers. For each of the 11 secondary ossification centers, the coordinates of the secondary ossification center may be derived from the coordinates of the maximum response pixel in a corresponding probability map. As used herein, the maximum response pixel may refer to the pixel having the maximum probability value (or pixel value) in the probability map. In some embodiments, the processing device 120 may determine coordinates of a pixel having the maximum probability value, and designate the determined coordinates as the position of a secondary ossification center corresponding to the probability map. In some embodiments, the processing device 120 may compare each pixel value with a pixel threshold (e.g., 0.2, 0.3, 0.4, 0.5, 0.6, etc.) in a probability map. The pixel threshold may be in the range of [0,1]. If a value of a pixel is less than or equal to the pixel threshold, the pixel value may be reset as 0. If the value of the pixel is greater than the pixel threshold, the pixel value may be retained. In this way, the processing device 120 may generate a new probability map. The new probability map may be represented in the form of a binary image. The processing device 120 may perform a weighted average for all pixels and corresponding pixel values (i.e., probability values) according to Equation (1). Then the processing device 120 may determine the coordinates of the secondary ossification center corresponding to the probability map. In some embodiments, the processing device 120 may generate a ROI image based on at least part of the positions of the secondary ossification centers. The ROI image may include a carpal region covering the primary ossification centers. The ROI image may be fed to the second OCL sub-model 707, then the second OCL sub-model 707 may output a plurality of probability maps for localizing the primary ossification centers. Similarly, the processing device 120 may determine the position of each primary ossification center based on the maximum response pixel in a probability map.

In some embodiments, the OCL model may use a V-Net architecture to localize the ossification centers. The V-Net architecture may at least include a plurality of convolutional layers for downsampling and a plurality of deconvolutional layers for upsampling. The V-Net architecture, for example, as described with reference to Milletari, Fausto et al, "V-net: Fully convolutional neural networks for volumetric medical image segmentation," may be selected, the contents of which are hereby incorporated by reference.

In 1604, the processing device (e.g., the BAA module 410 of the processing device 120) may estimate, based on the normalized bone age image and information related to the positions of the plurality of ossification centers, a bone age of the subject using a bone age assessment (BAA) model. In some embodiments, the BAA model may include an Inception-V3 network followed by one or more fully connected (FC) layers. As used herein, the inception-V3 network may be referred to as a first part of the BAA model, and the followed FC layers may be referred to as a second part of the BAA model.

Figure 17:
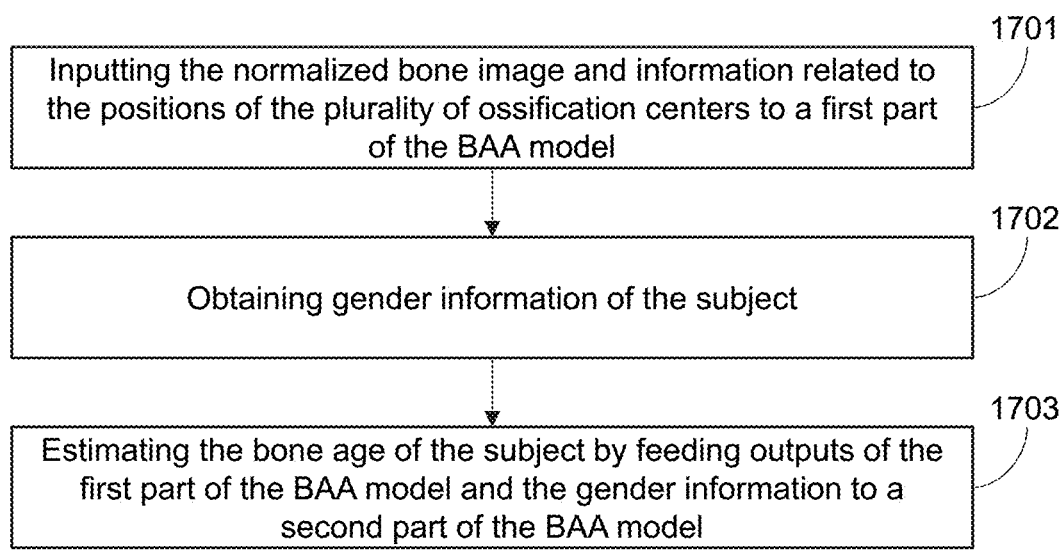
FIG. 17 is a flowchart illustrating an exemplary process for estimating a bone age of a subject according to some embodiments of the present disclosure.

Referring to FIG. 17, an exemplary process for estimating the bone age of the subject is illustrated. In 1701, the processing device (e.g., the BAA module 410) may input the normalized bone age image and information related to the positions of the plurality of ossification centers to a first part of the BAA model. The information related to the positions of the plurality of ossification centers may include the probability maps (e.g., the first batch of probability maps, the second batch of probability maps) indicative of the positions of the plurality of ossification centers (e.g., secondary ossification centers, primary ossification centers). In some embodiments, the first part of the BAA model may include a convolutional neural network, such as Inception-V3, VGG, ResNet, DenseNet, Inception-V4, and so on. As used herein, the first part of the BAA model may refer to an Inception-V3 network. In 1702, the processing device (e.g., the BAA module 410) may obtain gender information of the subject. In some embodiments, the gender information may be binary gender information (e.g., 0 for female and 1 for male, or vice versa). In some embodiments, the gender information may exist in the form of a gender vector. The gender vector may be generated by feeding the binary gender information to a connected layer (e.g., a 16-neuron FC layer). In 1703, the processing device (e.g., the BAA module 410) may estimate the bone age of the subject by feeding outputs of the first part of the BAA model (e.g., the Inception-V3 network) and the gender information to a second part of the BAA model. In some embodiments, the second part of the BAA model may refer to one or more fully connected (FC) layers that follows the Inception-V3 network. In some embodiments, the one or more FC layers may include the same or different number of neurons. Merely by way of example, the BAA module 410 may extract the outputs from the final FC layer of the Inception-V3 network, and concatenate the outputs with the gender vector. The concatenated result may be fed to the second part of the BAA model. Then the BAA model may output a bone age of the subject. More descriptions regarding the estimation of the bone age may be found elsewhere in the present disclosure (e.g., FIG. 18 and the descriptions thereof).

In 1605, the processing device (e.g., the report generation module 412 of the processing device 120) may generate one or more reports based on characteristic information of the subject, the positions of the plurality of ossification centers or the bone age. In some embodiments, the one or more reports may include at least one of a BAA report including BAA information or a growth assessment (GA) report including GA information for the subject, or a combined report including both BAA information and GA information. For example, the report generation module 412 may generate a report (e.g., the BAA report, the GA report) using a Natural Language Processing (NLP) technique. In some embodiments, the generated report may be a standardized report in accordance with a report template. The report may include a plurality of data items associated with the OCD and/or the BAA. The processing device may embed data regarding the plurality of data items to the reporting environment to generate a user readable report. For example, a report template describes that "the number of the ossification centers is X, positions of the ossification centers are Y, a predicted bone age is Z." Upon receipt of relevant data (e.g., X, Y, Z) output by the OCL model and/or the BAA model, the processing device 120 may apply the data into the report template.

Figure 20:
FIG. 20 is a schematic diagram illustrating an exemplary BAA report according to some embodiments of the present disclosure.

Referring to FIG. 20, an exemplary BAA report is illustrated. The BAA report may include results of the OCD and the BAA. For example, the BAA report may include the number (or count) of detected ossification centers and their respective positions. As shown in FIG. 20, the detected 20 ossification centers may be marked on the hand radiograph based on their respective positions. As another example, the BAA report may include the bone age prediction, for example, the predicted bone age is 6 years and 9 months. In some embodiments, the BAA report may also include characteristic information of the subject, such as height, actual age, gender, weight, and so on.

Figure 21:
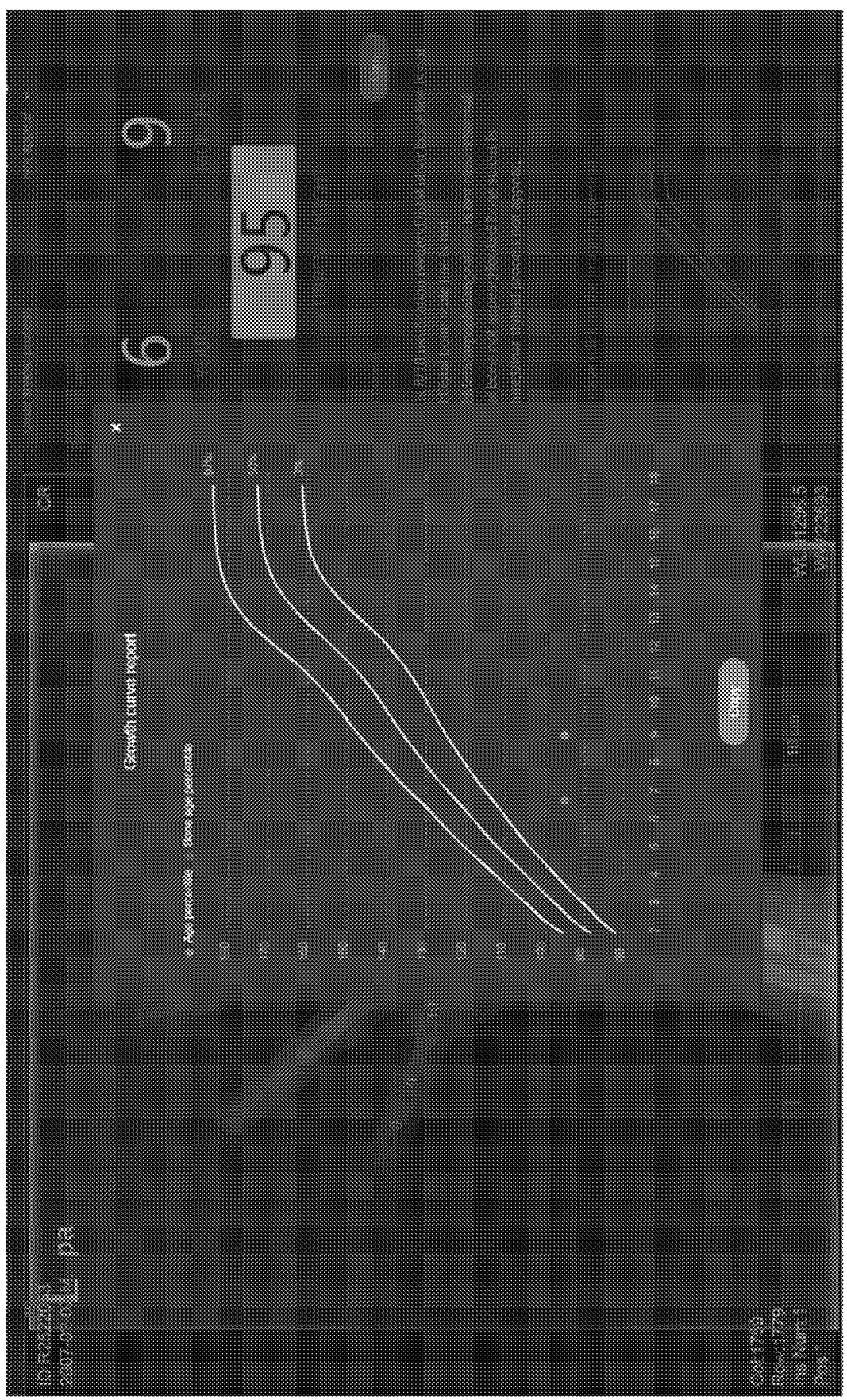
FIG. 21 is a schematic diagram illustrating an exemplary growth assessment (GA) report according to some embodiments of the present disclosure.

Referring to FIG. 21, an exemplary GA report is illustrated. The GA report may provide information or suggestions for the growth and/or development of the subject. For example, the GA report may include a growth curve, a predicted height, growth assessment information, or the like, or any combination thereof. In some embodiments, the growth assessment information may include a growth state. The growth state may be assessed based on a difference between the estimated bone age and the actual age. For example, if the estimated bone age is older than the actual age, the growth state of the subject may be labelled as "Advanced," which means the subject's growth and development is advanced relative to her/his actual age. If the estimated bone age is younger than the actual age, the growth state of the subject may be labelled as "Delayed," which means the subject's growth and development is delayed relative to her/his actual age. If the estimated bone age is equal to the actual age, the growth state of the subject may be labelled as "Normal," which means the subject's growth and development is at a normal level of her/his actual age. In some embodiments, the processing device 120 may obtain a standardized height and/or weight growth chart for children of a certain age or age range (0-18 years old) in a country. According to the standardized height and/or weight growth chart, the processing device 120 may determine the subject's height percentile and/or the weight percentile compared to, e.g., children of his/her age or age group. For example, if the percentile of the subject's current height is lower than a first value (e.g., 3%) in the growth chart for the same age group, the subject's height level is labelled as "Low," which means the subject's growth is slow. As another example, if the percentile of the subject's current height is greater than a second value (e.g., 97%) height and weight standardized growth chart, the subject's height level is labelled as "High," which means the subject's growth is better than most peers. It should be noted that the height level or the weight level may be labelled using different terms and not limited to those exemplified in the present disclosure. In some embodiments, the processing device 120 may predict an adult height of the subject based on empirical formulas, e.g.:

$$H_{man}=[(H_{dad}+H_{mom})\times 1.08]/2, \tag{2}$$

$$H_{woman}=[H_{dad}\times 0.923+H_{mom}]/2, \tag{3}$$

where $H_{man}$ and $H_{woman}$ represent predicted adult height for a male subject and a female subject, respectively, $H_{dad}$ and $H_{mom}$ represent actual heights of the subject's parents.

It should be noted that the descriptions in FIGS. 16 and 17 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further generate health suggestions or tips for the subject based on the generated report data.

Figure 18:
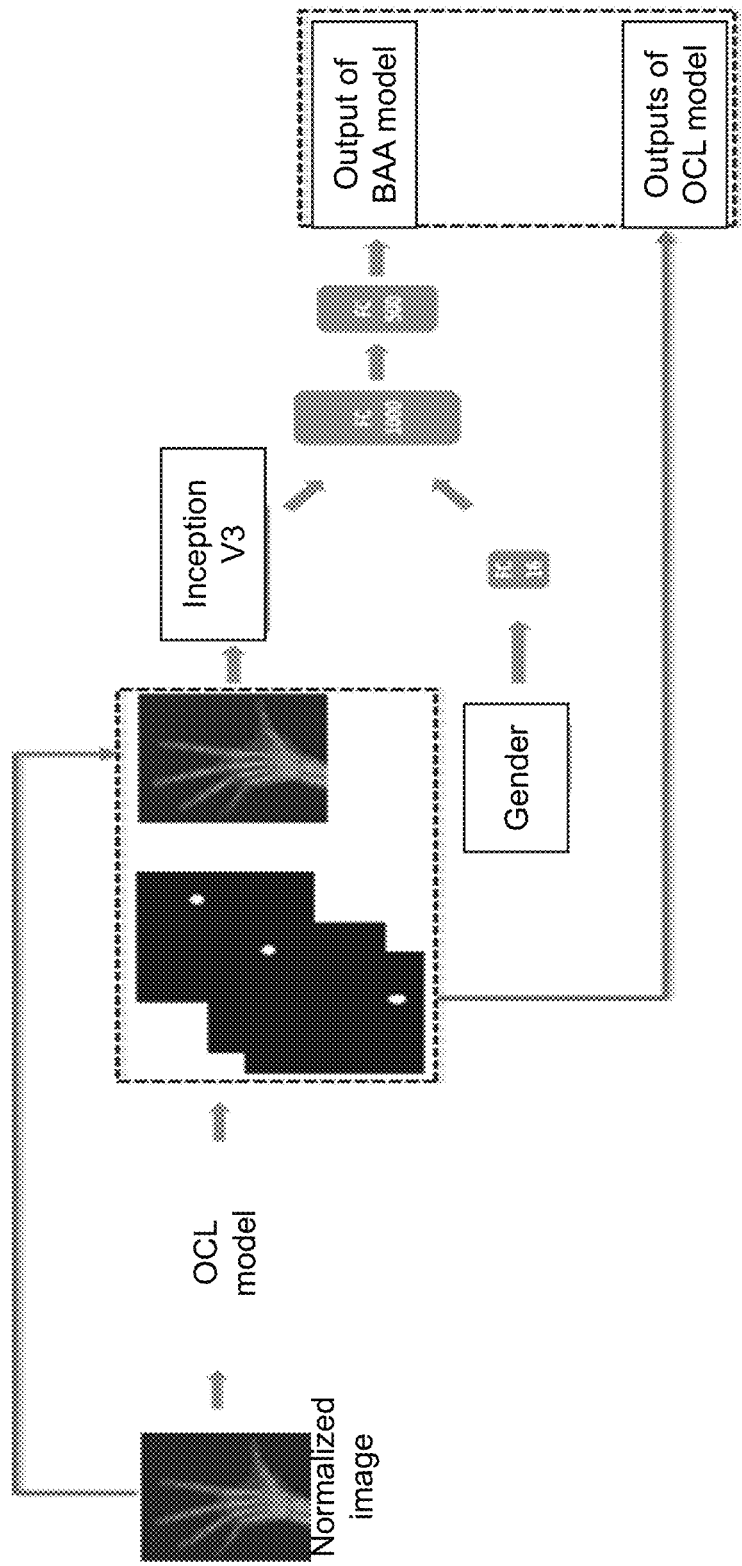
FIG. 18 is a schematic diagram illustrating a pipeline of ossification center detection (OCD) and bone age assessment (BAA) according to some embodiments of the present disclosure.

FIG. 18 illustrates a pipeline of ossification center detection (OCD) and bone age assessment (BAA) according to some embodiments of the present disclosure. As illustrated in FIG. 18, a normalized bone age image may be taken as an input of an OCL model. For example, a hand radiograph may be preprocessed (or normalized) to form the input normalized bone age image. The OCL model, such as a U-Net model or a V-Net model, may output a plurality of probability maps indicative of the positions of the ossification centers (e.g., the primary ossification centers and/or the second ossification centers). The positions of the ossification centers may be determined based on the output probability maps. The plurality of probability maps and the normalized bone age image may be input to a first part of a BAA model, such as an Inception-V3 network. Simultaneously or synchronously, binary gender information may be fed to a 16-neuron fully connected (FC) layer ("FC 16" shown in FIG. 18) to form a gender vector. The size of the formed gender vector may be 1×16. In some embodiments, for a male subject, the gender vector may be an all-one vector where every element is equal to one. For a female subject, the gender vector may be an all-zero vector where every element is equal to zero. Outputs of the final FC layer of the Inception V3 network and the gender vector may be concatenated. The concatenated result may be fed to one or more FC layers of a second part of the BAA model. As illustrated in FIG. 18, the second part of the BAA model may include a 1000-neuron FC layer ("FC 1000" shown in FIG. 18) followed by a 500-neuron layer ("FC 500" shown in FIG. 18). In some embodiments, each FC layer of the second part of the BAA model is followed by a "ReLU" unit. Finally, the BAA model may output a single predicted bone age from the output layer of the BAA model.

It should be noted that the formed gender vector may be not limited to the vector of 1×16. The gender vector may be set as a vector of any size, such as 1×32, 1×64, and so on. The size of the gender vector may be expressed as 1×N, where N is a positive integer.

Figure 19:
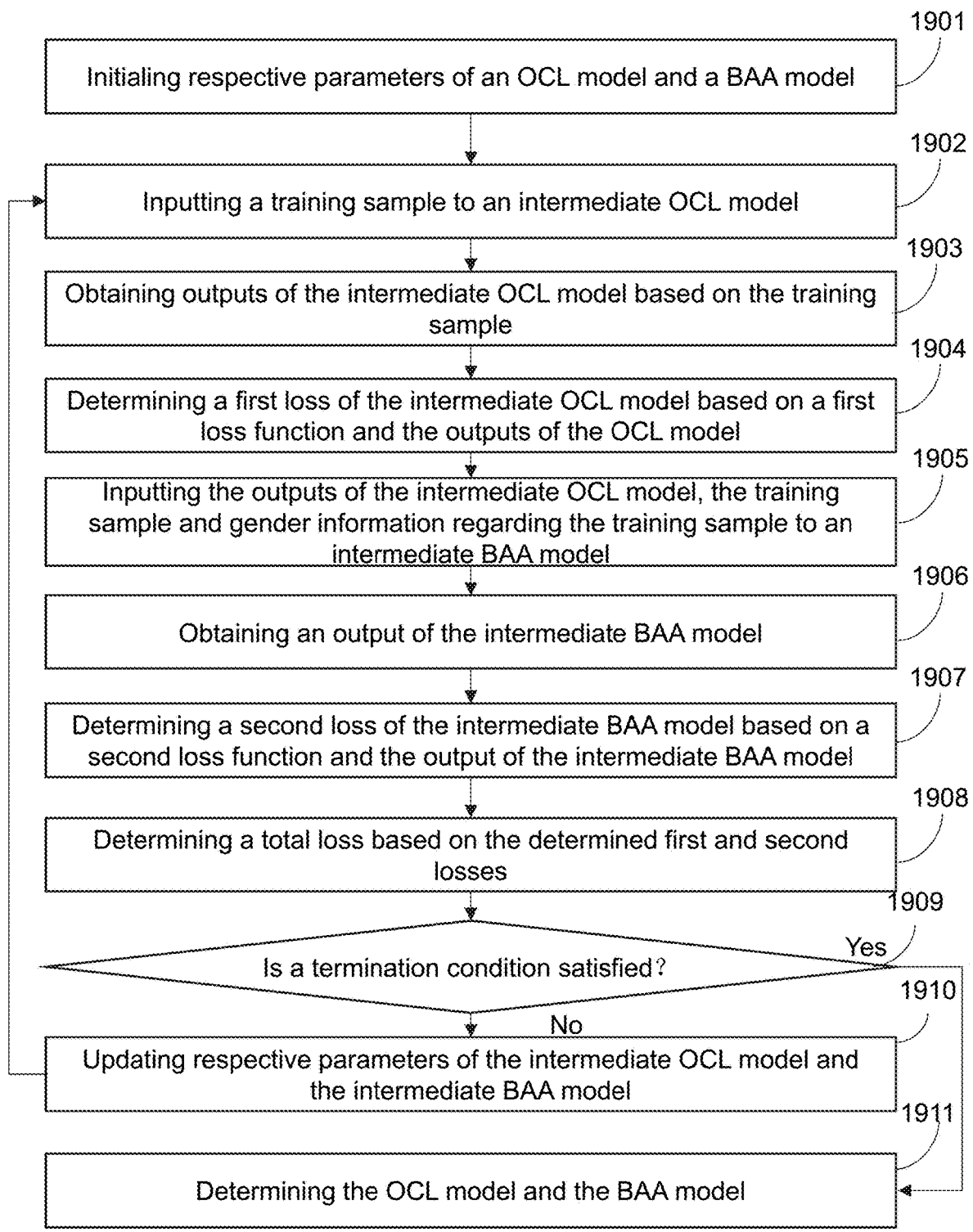
FIG. 19 is a flowchart illustrating an exemplary process for jointly training an ossification center localization (OCL) model and a bone age assessment (BAA) model according to some embodiments of the present disclosure.

FIG. 19 is a flowchart illustrating an exemplary process for jointly training an ossification center localization (OCL) model and a bone age assessment (BAA) model according to some embodiments of the present disclosure. In some embodiments, process 1900 may be executed by the image processing system 100. For example, the process 1900 may be implemented as a set of instructions (e.g., an application) stored in a storage device (e.g., the storage device 130, the storage 220, and/or the storage unit 370). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 1900. The operations of the illustrated process presented below are intended to be illustrative. In some embodiments, the process 1900 may be accomplished with one or more additional operations not described and/or without one or more of the operations discussed. Additionally, the order of the operations of process 1900 illustrated in FIG. 19 and described below is not intended to be limiting. In some embodiments, the OCL model and the BAA model described in present disclosure may be obtained according to the process 1900.

In 1901, the processing device (e.g., the training module 404 of the processing device 120) may initialize respective parameters of an OCL model and a BAA model.

In some embodiments, the OCL model and/or the BAA model may use a fully convolutional network (FCN) architecture, such as U-Net, V-Net, Inception-V3, etc., respectively. For example, the OCL model may use the U-Net architecture described in connection with FIG. 7, or the V-Net architecture described in connection with FIG. 16. The BAA model may be composed of two parts, for example, the Inception-V3 network and one or more FC layers connected to the Inception-V3 network described in connection with FIG. 18. In respective network architectures of the OCL model and the BAA model, a plurality of architecture parameters and a plurality of learning parameters may be initialized. Exemplary architecture parameters of the OCL model and/or the BAA model may include the size of a convolutional kernel, the number (or count) of layers, the number (or count) of nodes (or neurons) in each layer, a learning rate, a minibatch size, an epoch, etc. Exemplary learning parameters of the OCL model and/or the BAA model may include a connected weight between two connected nodes, a bias vector related to a node, etc. The connected weight between two connected nodes may be configured to represent a proportion of an output value of a node to be used as an input value of another connected node.

In some embodiments, the connected weights of the OCL model and/or the BAA model may be initialized to be random values in a range, e.g., the range from −1 to 1. In some embodiments, all the connected weights of the OCL model and/or the BAA model may have the same value in the range from −1 to 1, for example, 0. The bias vector related to a node may be configured to control an output value of the node deviating from an origin. In some embodiments, the bias vector of nodes in the OCL model and/or the BAA model may be initialized to be random values in a range from 0 to 1. In some embodiments, the parameters of the OCL model and/or the BAA model may be initialized based on a Gaussian random algorithm, a Xavier algorithm, etc. In some embodiments, the OCL model and/or the BAA model including the initialized parameters may be deem as a preliminary OCL model and/or BAA model. The preliminary OCL model and the preliminary BAA model may be iteratively trained jointly based on a plurality of training samples. During the training process, an intermediate OCL model and an intermediate BAA model may be generated after each iteration, and their parameters may be further updated in subsequent iterations of the training process. Each iteration may include operation 1902-1910 described as below.

In 1902, in one iteration, the processing device (e.g., the training module 404 of the processing device 120) may input a training sample to an intermediate OCL model. The intermediate OCL model may be the preliminary OCL model for the first iteration or an intermediate OCL model generated in a preceding iteration.

In some embodiments, the plurality of training samples may be collected as training data for jointly training the OCL model and the BAA model. Each training sample may be a bone age image from a subject (e.g., a patient). For example, the bone age image may be an X-ray image of a hand (e.g., a hand radiograph). The plurality of training samples may include hand radiographs for female and hand radiographs for male. In some embodiments, the plurality of training samples may be collected from at least one public dataset (e.g., RSNA bone age dataset) and/or at least one private dataset (e.g., a local hospital dataset). In some embodiments, each training sample can be labelled. For example, positions (coordinates) of landmarks of the ossification centers (e.g., the secondary ossification centers in a carpal region) may be labelled to form a label dataset. The label data of a landmark also referred to as landmark ground truth. As another example, each training sample may be labelled by skeletal bone age, that is, bone age ground truth. In some embodiments, the plurality of training samples may be normalized in advance before the training. For example, each hand radiograph may be normalized to a fixed image size (512× 512 pixels). In some embodiments, the processing device 120 may preprocess the plurality of training samples to normalize the training samples in accordance with the preprocessing procedure described in FIG. 9. In some embodiments, for data augmentation, each training sample may be randomly translated and rotated. By the normalization and the data augmentation, it may facilitate to reduce false positive rate of the ossification center detection and improve the robustness of the model.

In 1903, the processing device (e.g., the training module 404 of the processing device 120) may obtain outputs of the intermediate OCL model based on the training sample. As described in connection with FIG. 18, the intermediate OCL model may generate a plurality of probability maps indicative of the plurality of ossification centers by processing the input training sample, such as extracting feature maps by a plurality of convolutional layers in the intermediate OCL model.

In 1904, the processing device (e.g., the training module 404 of the processing device 120) may determine a first loss of the intermediate OCL model based on a first loss function and the outputs of the intermediate OCL model. In some embodiments, the first loss function may include a relative error (RE) loss function, a mean absolute error (MAE) loss function, a focal loss function, a log loss function, a cross-entropy loss function, a Dice loss function, etc. For example, the MAE loss function may be designated as the first loss function of the intermediate OCL model. As another example, the focal loss function may be designated as the first loss function of the intermediate OCL model. The first loss function may be described with reference to Equation (6). According to the first loss function, the processing device 120 may determine the first loss in a current iteration.

In 1905, the processing device (e.g., the training module 404 of the processing device 120) may input the outputs of the intermediate OCL model, the training sample and gender information regarding the training sample to an intermediate BAA model. The intermediate BAA model may be the preliminary BAA model for the first iteration or an intermediate BAA model generated in a preceding iteration. As described in connection with FIG. 18, the outputs of the intermediate OCL model (e.g., the probability maps) and the training sample (e.g., the input hand radiograph) may be input to the Inception-V3 network of the BAA model. In some embodiments, the gender vector of the gender information and outputs of the final FC layer of the Inception-V3 network may be concatenated. The concatenated result may be input to one or more FC layers of the intermediate BAA model.

In 1906, the processing device (e.g., the training module 404 of the processing device 120) may obtain an output of the intermediate BAA model (e.g., an estimated bone age).

In 1907, the processing device (e.g., the training module 404 of the processing device 120) may determine a second loss of the intermediate BAA model based on a second loss function and the output of the intermediate BAA model. In some embodiments, the second loss function and the first loss function may be the same or different. For example, the second loss function may include a relative error (RE) loss function, a mean absolute error (MAE) loss function, a focal loss function, a log loss function, a cross-entropy loss function, a Dice loss function, etc. For example, the second loss function may use a focal loss function as well. As another example, the second loss function may use the RE loss function as defined by Equation (7). According to the second loss function, the processing device 120 may determine the second loss in the current iteration.

In 1908, the processing device (e.g., the training module 404 of the processing device 120) may determine a total loss based on the determined first and second losses. In some embodiments, the total loss function may be a linear combination of the first loss function and the second loss function. For example, the total loss may be a weighted sum of the first loss and the second loss. In some embodiments, the total loss function may be defined as follows:

$$L_{total}=a_1 \times L_1 + a_2 \times L_2, \quad (4)$$

where $L_{total}$, $L_1$, and $L_2$ represent a total loss, a first loss of the intermediate OCL model and a second loss of the intermediate BAA model, respectively. $\alpha_1$ and $\alpha_2$ represent a weight factor of the first loss and the second loss, respectively. For example, if the OCD and the BAA are deemed of equal importance, $\alpha_1=\alpha_2=0.5$. According to the total loss function, the processing device 120 may determine the total loss in the current iteration.

In 1909, the processing device (e.g., the training module 404 of the processing device 120) may determine whether a termination condition is satisfied. In some embodiments, if the termination condition is satisfied, the processing device 120 may proceed to operation 1911 and complete the iterative process. If the termination condition is not satisfied, the processing device 120 may proceed to operation 1910 and perform a next iteration. The termination condition may provide an indication of whether the intermediate OCL model and the intermediate BAA model are sufficiently trained.

In some embodiments, the termination condition may be satisfied if the total loss is equal to or less than a threshold (e.g., a constant). In some embodiments, the termination condition may be satisfied if the total loss converges. For example, the total loss may be considered converged when the variation of the total losses (e.g., the values of the total loss function) in two or more consecutive iterations is equal to or less than a threshold (e.g., a constant). In some embodiments, the termination condition may be satisfied when a specified iteration number (or count), such as a maximum iteration count, is performed in the training process.

In 1910, the processing device (e.g., the training module 404 of the processing device 120) may update respective parameters of the intermediate OCL model and the intermediate BAA model. In some embodiments, the processing device 120 may synchronously update at least one learning parameter of the intermediate OCL model and/or the intermediate BAA model using a back-propagation (BP) algorithm. Exemplary BP algorithms may include a stochastic gradient descent (SGD) algorithm, an Adam algorithm, an Adagrad algorithm, an Adadelta algorithm, an RMSprop algorithm, or the like, or a combination thereof. For example, the training module 404 may update the parameters of the intermediate OCL model and the intermediate BAA model using the SGD algorithm.

In 1911, the processing device (e.g., the training module 404 of the processing device 120) may determine the OCL model and the BAA model. In some embodiments, the OCL model and the BAA model may be determined based on respective updated parameters. The trained OCL model and the BAA model may be invoked to localize the ossification centers and estimate the bone age of the subject from the bone age image.

In some embodiments, process 1900 may be repeated with respect to the plurality of training samples to improve or optimize the OCL model and the BAA model until the termination condition is satisfied. In different rounds of process 1900, different training samples may be inputted to an intermediate OCL model and an intermediate BAA model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 1902 and 1903 may be integrated into a single operation. As another example, operations 1906 and 1907 may be integrated into a single operation.

Figure 22:
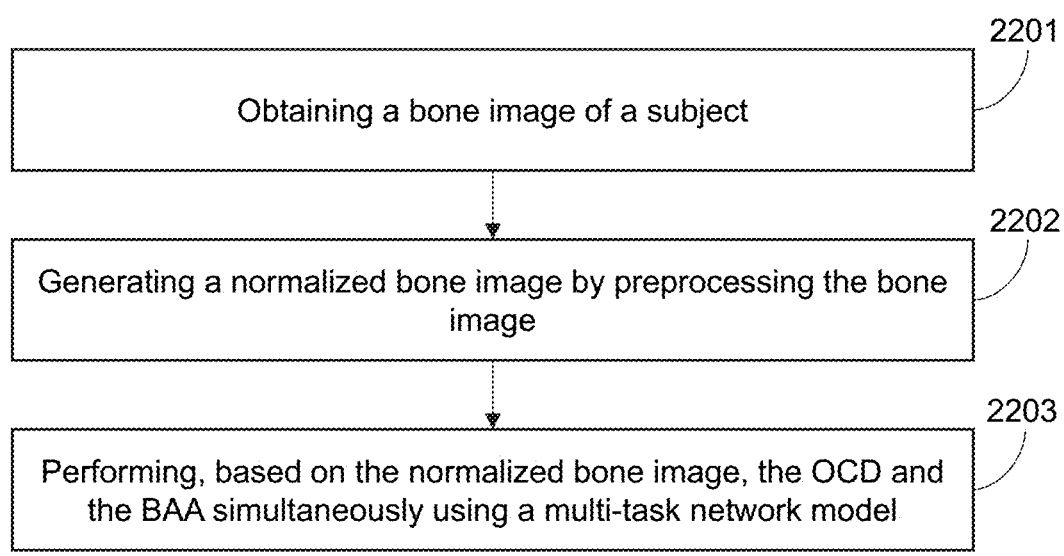
FIG. 22 is a flowchart illustrating an exemplary process for ossification center detection (OCD) and bone age assessment (BAA) according to some embodiments of the present disclosure.

FIG. 22 is a flowchart illustrating an exemplary process for ossification center detection (OCD) and bone age assessment (BAA) according to some embodiments of the present disclosure. In some embodiments, process 2200 may be executed by the image processing system 100. For example, the process 2200 may be implemented as a set of instructions (e.g., an application) stored in a storage device (e.g., the storage device 130, the storage 220, and/or the storage unit 370). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 2200.

The operations of the illustrated process presented below are intended to be illustrative. In some embodiments, the process 2200 may be accomplished with one or more additional operations not described and/or without one or more of the operations discussed. Additionally, the order of the operations of process 2200 illustrated in FIG. 22 and described below is not intended to be limiting.

In 2201, the processing device (e.g., the acquisition module 402 of the processing device 120) may obtain a bone age image (e.g., a hand radiograph) of a subject (e.g., a child). The bone age image may be used for the OCD and the BAA. The descriptions regarding the bone age image may be found elsewhere in the present disclosure and not be repeated herein. See, e.g., operation 601 in FIG. 6 or operation 1601 in FIG. 16.

In 2202, the processing device (e.g., the preprocessing module 414 of the processing device 120) may generate a normalized bone age image by preprocessing the bone age image. In some embodiments, the preprocessing may include but not limited to segmenting a target region (e.g., the hand/wrist region), adjusting a position of the target region in the image, resizing the image size, and normalizing the grayscale base of the image. For example, the processing device 120 may perform the preprocessing as the preprocessing procedure described in FIG. 9. After the preprocessing procedure, the normalized bone age image (e.g., a normalized gray-scale bone age image) may be generated.

In 2203, the processing device (e.g., the OCC module 406, the OCL module 408 and/or the BAA module 410 of the processing device 120) may perform, based on the normalized bone age image, the OCD and the BAA simultaneously using a multi-task network model. For example, the processing device 120 may take the normalized bone age image as an input of the multi-task network model. One or more subnets of the multi-task network model may perform one or more tasks of the OCD and the BAA simultaneously by extracting feature maps of the input image. In some embodiments, the OCD may include a classification and a localization for a plurality of ossification centers, that is, ossification center classification and ossification center localization. In some embodiments, the multi-task network model may be a multi-task convolutional neural network (CNN). For example, the multi-task network model may use an FCN architecture. Exemplary FCN may include U-Net, V-Net, M-Net, a Visual Geometry Group (VGG) network, a residual neural network (ResNet), a dense neural network (DenseNet), or the like, or any combination thereof. In some embodiments, the multi-task network model may include two or more of a first subnet, a second subnet, and a third subnet. The first subnet (also referred to as "landmark classification subnet") may be configured to classify a plurality of ossification centers. The second subnet (also referred to as "landmark localization subnet") may be configured to localize positions of the plurality of ossification centers. The third subnet (also referred to as "bone age assessment subnet) may be configured to estimate a bone age of a subject. In some embodiments, the multi-task network model may include a backbone network connected to at least one of the first subnet, the second subnet, and the third subnet. For example, the backbone network may use a U-Net architecture.

Figure 23:
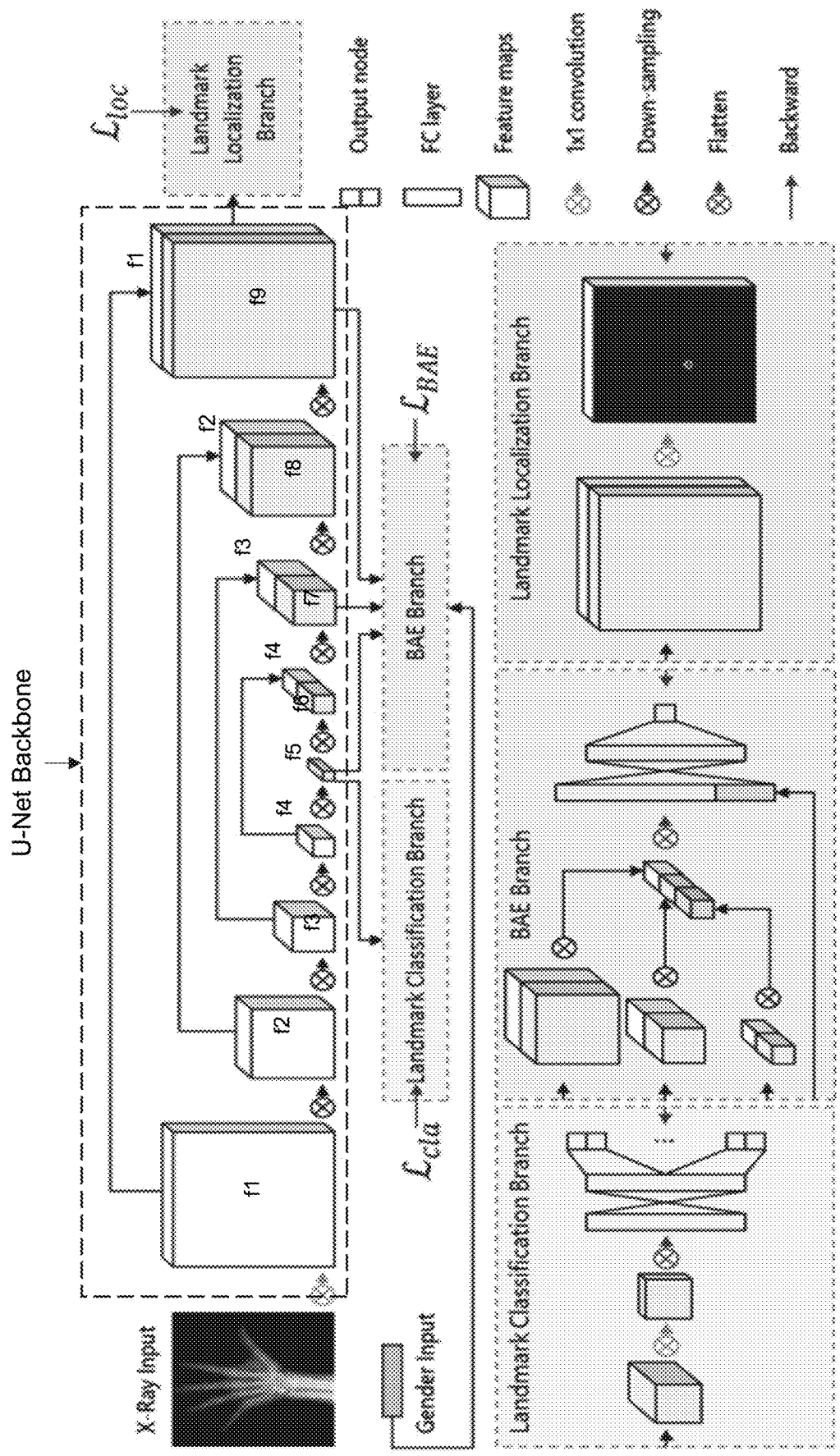
FIG. 23 is a schematic diagram illustrating an architecture of an exemplary multi-task network model according to some embodiments of the present disclosure.

Referring to FIG. 23, an architecture of an exemplary multi-task network model is illustrated. The multi-mask network model may include a U-Net backbone network and three task-specific subnetworks, such as a landmark localization branch (i.e., the landmark localization subnet), a landmark classification branch (i.e., the landmark classification subnet), and a BAE branch (i.e., the bone age assessment subnet). As used herein, the BAE branch may also be referred to as the BAA branch. In some embodiments, the U-Net backbone may include a top-down contracting path and a bottom-up expanding path that are symmetric (not shown in FIG. 23). As illustrated in FIG. 22, feature maps from the contracting path and the expanding path are connected. The contracting path may be responsible for extracting feature maps through down-sampled convolutional layers. The resolution of a feature map may be reduced at the end of each stage of the contracting path. For example, the resolution of an output feature map may be halved than an input feature map at a stage of the contracting path. The symmetric expanding path may be responsible for increasing the resolution of the feature maps from the contracting path until the original resolution is reached.

As illustrated in FIG. 23, in the contracting path, feature maps f1 may be extracted from the input X-ray bone age image through a 1×1 convolution. The feature maps f1 may include a plurality of feature maps. A feature map may also be referred to as a feature channel. The resolution of each of the feature maps f1 may be equal to that of the input X-ray bone age image. Feature maps f2 may be extracted from the feature maps f1 through a down-sampling convolution. In some embodiments, the resolution of each of the feature maps f2 may be the half of the resolution of the input feature maps f1. Similarly, feature maps f3 may be extracted from feature maps f2, feature maps f4 may be extracted from feature maps f3, and feature maps f5 may be extracted from the feature maps f4. The expanding path may be connected to an end of the contracting path. The feature maps f5 may be final outputs of the contracting path as well as initial inputs of the expanding path. In the symmetric expanding path, feature maps f6 may be obtained based on feature maps f5 through an up-sampling convolution. In some embodiments, the resolution of the feature maps f6 may be equal to that of the feature maps f4. In this stage, the feature maps f6 and the feature maps f4 may be concatenated due to the same resolution. The number (or count) of channels of the concatenated feature maps may be doubled when the feature maps f4 and the feature maps f6 are concatenated. The concatenated feature maps may be input to a next stage as a whole. Similarly, feature maps f7 may be obtained through the up-sampling convolution of the input concatenated feature maps generated by concatenating the feature maps f6 and the feature maps f4. The feature maps f7 and the feature maps f3 may be concatenated. Feature maps f8 may be obtained through the up-sampling convolution of the input concatenated feature maps generated by concatenating the feature maps f7 and the feature maps f3. The feature maps f8 and the feature maps f2 may be concatenated. Feature maps f9 may be obtained through the up-sampling convolution of the input concatenated feature maps generated by concatenating the feature maps f8 and the feature maps f2. The feature maps f9 and the feature maps f1 may be concatenated. It is understood that the number (or count) of channels of the concatenated feature maps may be doubled when two same resolution feature maps are concatenated. The resolution of the feature maps f9 may be restored to the original resolution of the input X-ray image.

In some embodiments, the landmark classification subnet (e.g., the landmark classification branch in a dotted box) may be built on the final layer of the contracting path. For example, feature maps f5 may be fed to the landmark classification subnet for classifying the ossification centers. In some embodiments, the landmark localization subnet (e.g., the landmark localization branch in a dotted box) may be built on the final layer of the expanding path. For example, the feature maps composed of feature maps f9 and f1 may be fed to the landmark localization subnet for localizing positions (or coordinates) of the ossification centers. In some embodiments, for the bone age assessment subnet (e.g., the BAE branch in a dotted box) may be designed to connect to one or more layers of the expanding path such that the bone age assessment subnet may utilize one or more feature maps generated by one or more layers of the expanding path. For example, feature maps f5, the feature maps composed of feature maps f7 and f3, and the feature maps composed of feature maps f9 and f1 may be fed to the bone age assessment subnet for estimating a bone age of a subject. The landmark localization subnet, the landmark classification subnet, and the bone age assessment subnet may share at least part of feature maps generated by the U-Net backbone network, which may improve a computing efficiency of the multi-task network model.

In some embodiments, the multi-task network model may use the V-Net architecture as described with reference to Chinese patent application No. CN 201910886148.2. The V-Net based multi-task network model may include a first subnet for ossification center classification, a second subnet for ossification center localization, and a third network for bone age assessment. The first subnet may include one or more downsampling convolutional layers, such as three downsampling layers. The first subnet may include the contracting path of the V-Net architecture. In each stage of the contracting path, downsampled feature maps may be obtained. The first subnet may output the ossification center classification result by processing the downsampled feature maps. The second subnet may include one or more upsampling convolutional layers, such as three upsampling layers. The second subnet may include the expanding path of the V-Net architecture. Similar to the procedure of the expanding path of the U-Net backbone network of the multi-task network model illustrated in FIG. 23, in the second subnet, the downsampled feature maps may be concatenated to corresponding upsampled feature maps from each of the one or more upsampling layers. The resolution of the feature maps of the final layer of the second subnet may be restored to the original resolution of the input bone age image. The second subnet may output the ossification center localization result by processing the feature maps of the final layer of the second subnet. The third subnet may include one or more downsampling layers and a bottle neck layer. The third subnet may process the concatenated feature maps from each stage of the second network to estimate the bone age. In some embodiments, for the V-Net based multi-task network model, a total loss may be a linear combination of a first loss of the first subnet, a second loss of the second subnet and a third loss of the third subnet. It should be noted that the idea of the multi-task network model may be used for processing multiple tasks, not only for the ossification center classification, the ossification center localization and the bone age assessment. For example, the multiple tasks may include image-level classification or regression tasks and/or pixel-level classification or regression tasks. The image-level classification or regression tasks and/or pixel-level classification or regression tasks may include image segmentation, image localization, image classification, and so on. In some embodiments, the first subnet may be used for performing image-level tasks. The first subnet may downsample an input image through the downsampling convolutional layers of the first network. The downsampled feature maps may be obtained and used for generating a first image-level result (e.g., an image classification result). The downsampled feature maps may input the second subnet of the multi-task network model. The second subnet may upsample the input downsampled feature maps. The upsampled feature maps corresponding to the downsampled feature maps may be obtained. In some embodiments, the second subnet may be used for performing pixel-level tasks. For example, in each stage of the second subnet, the downsampled feature maps and the corresponding upsampled feature maps may be concatenated together due to the same resolution. The second subnet may process the concatenated feature maps to generate a pixel-level result (e.g., an image localization result). In some embodiments, the concatenated feature maps of each stage of the second subnet may be input to the third subnet of the multi-task network model. The resolutions of the concatenated feature maps in each stage of the second subnet may be different. Through downsampling convolutional layers of the third subnet, the resolutions of the concatenated feature maps may be normalized to the same resolution. The third subnet may process the feature maps having the same resolution to generate a second image-level result (e.g., an image regression result). More descriptions regarding the multi-task network model can be described with reference to Chinese patent application No. CN 201910886148.2, the contents of which are hereby incorporated by reference.

Figure 24:
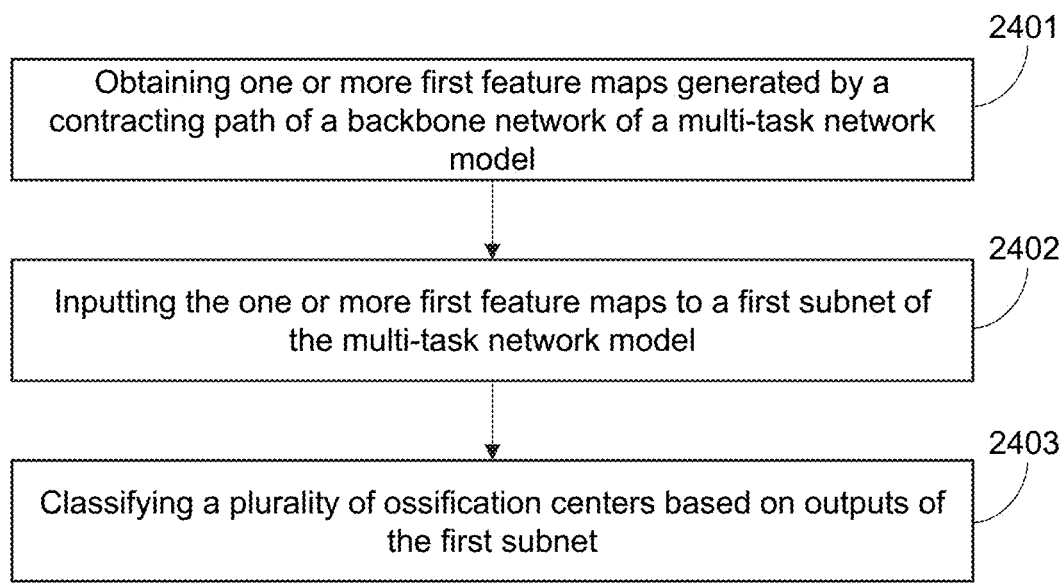
FIG. 24 is a flowchart illustrating an exemplary process for ossification center classification according to some embodiments of the present disclosure.

FIG. 24 is a flowchart illustrating an exemplary process for ossification center classification according to some embodiments of the present disclosure.

In 2401, the processing device (e.g., the OCC module 406 of the processing device 120) may obtain one or more first feature maps generated by a contracting path of a backbone network of a multi-task network model (e.g., the multi-task network model described in FIG. 23). As described in connection with FIG. 23, the feature maps f5 may be generated by the final layer of the contracting path. The feature maps f5 may include one or more first feature maps. In 2402, the processing device (e.g., the OCC module 406 of the processing device 120) may input the one or more first feature maps to a first subnet of the multi-task network model. The first subnet may refer to the landmark classification subnet described in FIG. 23. In some embodiments, the first subnet may be deemed as a neural-network based classifier. For example, the first subnet may include one or more down-sampled convolutional layers and one or more FC layers. In 2403, the processing device (e.g., the OCC module 406 of the processing device 120) may classify a plurality of ossification centers based on outputs of the first subnet. In some embodiments, the input first feature maps may be gradually down-sampled to the lowest resolution feature maps through the one or more convolutional layers. The lowest resolution feature maps may be flattened and fed to the one or more FC layers. The first subnet may output classification results after the one or more FC layers. The classification results may be indicative of what kind of ossification center, e.g., a primary ossification center, a secondary ossification center, that the detected landmark belongs to.

Figure 25:
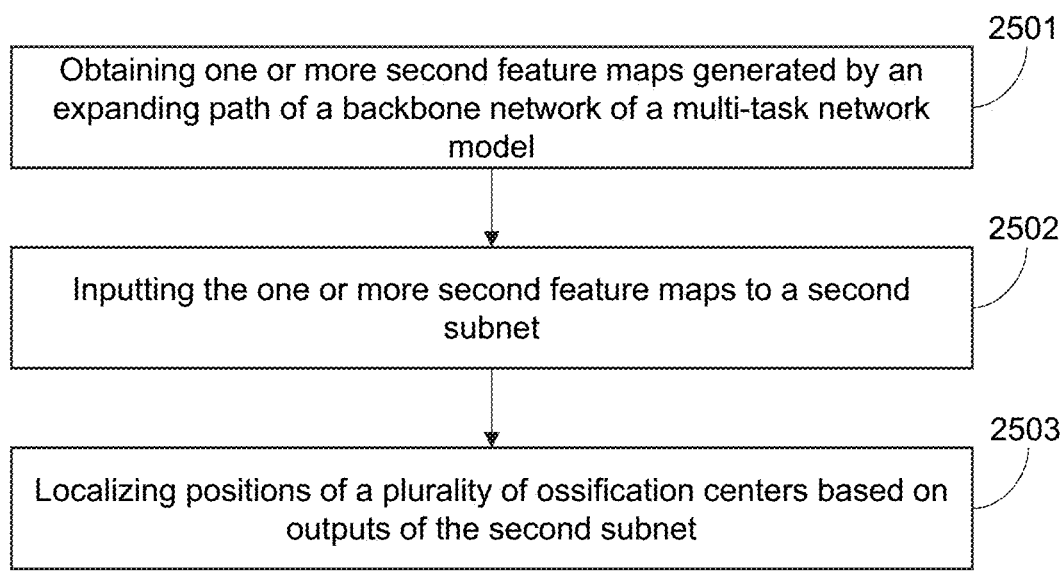
FIG. 25 is a flowchart illustrating an exemplary process for ossification center localization according to some embodiments of the present disclosure.

FIG. 25 is a flowchart illustrating an exemplary process for ossification center localization according to some embodiments of the present disclosure.

In 2501, the processing device (e.g., the OCL module 408 of the processing device 120) may obtain one or more second feature maps generated by an expanding path of a backbone network of a multi-task network model (e.g., the multi-task network model described in FIG. 23). As described in connection with FIG. 23, the concatenated feature maps (including feature maps f9 and features map f1) may be generated by the final layer of the expanding path. The concatenated feature maps may include the one or more second feature maps. In 2502, the processing device (e.g., the OCL module 408 of the processing device 120) may input the one or more second feature maps to a second subnet of the multi-task network model. The second subnet may refer to the landmark localization subnet described in FIG. 23. In some embodiments, the second subnet may be deemed as a pixel-level classifier based on neural networks. The second subnet may include one or more convolutional layers (e.g., 1×1 convolutional layer(s)). In 2503, the processing device (e.g., the OCL module 408 of the processing device 120) may localize positions of a plurality of ossification centers based on outputs of the second subnet. In some embodiments, the one or more second feature maps may be processed by the one or more convolutional layers of the second subnet. Followed by the one or more convolutional layers, a plurality of probability maps may be output by the second subnet. The output probability maps may be indicative of the positions of the plurality of ossification centers. The processing device 120 may determine the positions (or coordinates) of the plurality of ossification centers based on the probability maps. For example, the coordinates of an ossification center may be derived from the coordinates of a maximum response pixel in a probability map.

Figure 26:
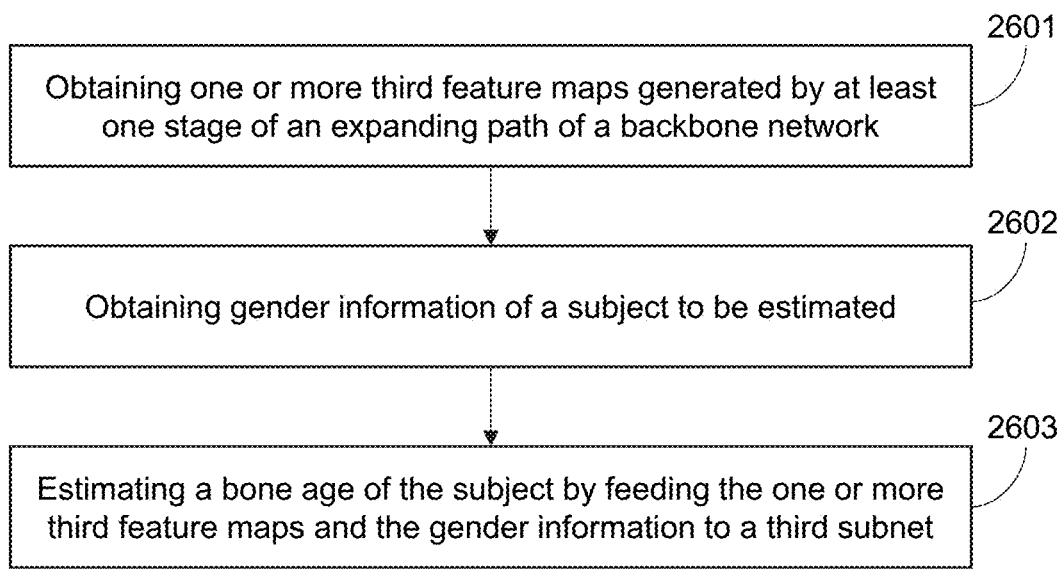
FIG. 26 is a flowchart illustrating an exemplary process for the bone age assessment according to some embodiments of the present disclosure.

FIG. 26 is a flowchart illustrating an exemplary process for the bone age assessment according to some embodiments of the present disclosure.

In 2601, the processing device (e.g., the BAA module 410 of the processing device 120) may obtain one or more third feature maps generated by at least one stage of an expanding path of a backbone network of a multi-task network model (e.g., the multi-task network model described in FIG. 23). As described in connection with FIG. 23, in the expanding path, in different stages of the backbone network, different resolution feature maps may be generated, such as the feature maps f5, f6, f7, f8, and f9. The processing device 120 may obtain the multi-resolution feature maps gathered from different stages of the backbone network. For example, the BAA module 410 may obtain the feature maps from one or more stages of the expanding path. As another example, the processing device 120 may obtain the feature maps from all stages of the expanding path. The obtained feature maps may be designated as the third feature maps that include the one or more third feature maps. In 2602, the processing device (e.g., the BAA module 410 of the processing device 120) may obtain gender information of a subject to be estimated. In some embodiments, the gender information may be binary gender information (e.g., 0 for female and 1 for male). In some embodiments, the gender information may exist in the form of a gender vector. For example, for a male subject, the gender vector may be an all-one vector where every element is equal to one. For a female subject, the gender vector may be an all-zero vector where every element is equal to zero. In 2603, the processing device (e.g., the BAA module 410 of the processing device 120) may estimate a bone age of the subject by feeding the one or more third feature maps and the gender information to a third subnet of the multi-task network model. The third subnet may refer to the bone age assessment subnet (e.g., the BAE Branch) described in FIG. 23. In some embodiments, the third subnet may be deemed as a regression network, for example, a ResNet-style CNN with a regression output. In some embodiments, in the third subnet, the input multi-resolution third feature maps may be down sampled to the same resolution before fed into one or more FC layers of the third subnet. The processing device 120 may flatten the feature maps having a same resolution. The processing device 120 may embed the gender vector and the flattened feature data into the first FC layer of the one or more FC layers. After the one or more FC layers, the third subnet may output an estimated bone age.

Figure 27:
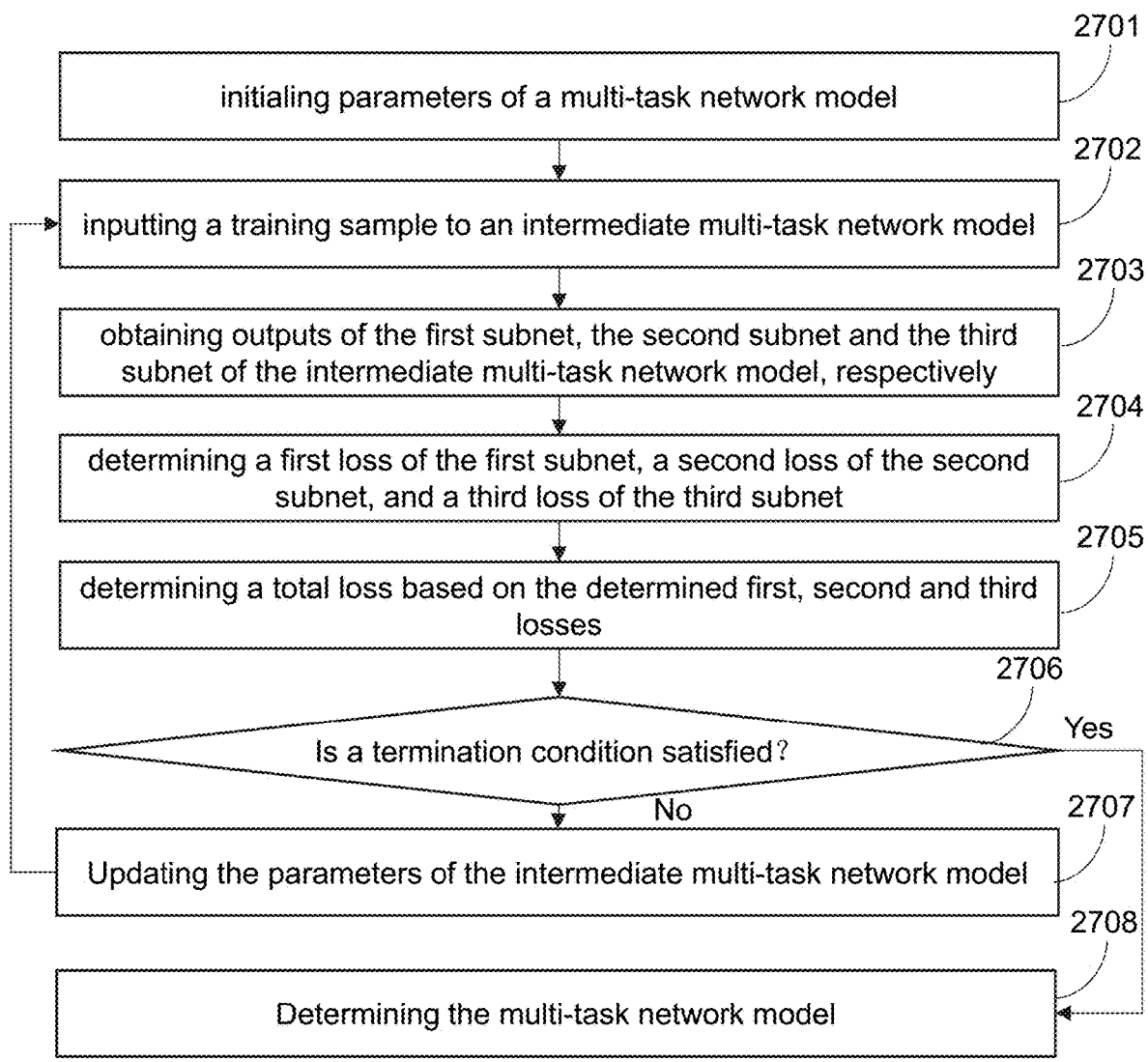
FIG. 27 is a flowchart illustrating an exemplary process for training a multi-task network model according to some embodiments of the present disclosure.

FIG. 27 is a flowchart illustrating an exemplary process for training a multi-task network model according to some embodiments of the present disclosure. In some embodiments, process 2700 may be executed by the image processing system 100. For example, the process 2700 may be implemented as a set of instructions (e.g., an application) stored in a storage device (e.g., the storage device 130, the storage 220, and/or the storage unit 370). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 2700. The operations of the illustrated process presented below are intended to be illustrative. In some embodiments, the process 2700 may be accomplished with one or more additional operations not described and/or without one or more of the operations discussed. Additionally, the order of the operations of process 2700 illustrated in FIG. 27 and described below is not intended to be limiting. In some embodiments, the multi-task network model described in connection with FIG. 22 or FIG. 23 may be obtained according to the process 2700.

The processing device (e.g., the processing device 120) may train the multi-task network model using a plurality of training samples. Merely by way of example, the multi-task network model may have the architecture illustrated in FIG. 23. Parameters of the multi-task network model may be optimized by minimizing a total loss function. The total loss function may be composed of a first loss function of the first subnet, a second loss function of the second subnet, and a third loss function of the third subnet. The three subnets of the multi-task network model may be jointly trained with respect to the total loss function. In some embodiments, the processing device (e.g., the training module 404 of the processing device 120) may iteratively update the parameters of the multi-task network model. More descriptions regarding the training of the multi-task network model may be found as below.

In 2701, the processing device (e.g., the training module 404 of the processing device 120) may initialize parameters of a multi-task network model. Architecture parameters and learning parameters of the multi-task network model may be initialized. For example, if the multi-task network model is trained using an Adam optimizer (learning rate=0.0001), the parameters of Adam have default values according to PyTorch. More descriptions regarding the architecture parameters and learning parameters may be found elsewhere in the present disclosure (e.g., FIG. 19, and the descriptions thereof).

In some embodiments, the multi-task network model including the initialized parameters may be deem as a preliminary multi-task network model. The preliminary multi-task network model may be iteratively trained based on a plurality of training samples. During the training process, an intermediate multi-task network model may be generated after each iteration, and their parameters may be further updated in subsequent iterations of the training process. Each iteration may include operation 2702-2707 described as below.

In 2702, in one iteration, the processing device (e.g., the training module 404 of the processing device 120) may input a training sample to an intermediate multi-task network model. The intermediate multi-task network model may be the preliminary multi-task network model for the first iteration or an intermediate multi-task network model generated in a preceding iteration. In some embodiments, the training sample may include a hand radiograph for a male or a hand radiograph for female. The description of a training sample with reference to operation 1902 in FIG. 19 is applicable here, and not repeated.

In 2703, the processing device (e.g., the training module 404 of the processing device 120) may obtain outputs of the first subnet, the second subnet, and the third subnet of the intermediate multi-task network model, respectively. As described in connection with FIG. 23, the first subnet may output a plurality of classification results (e.g., a plurality of probability values for predicting the ossification centers), the second subnet may output a plurality of probability maps indicative of the positions of the ossification centers, and the third subnet may output an estimated bone age.

In 2704, the processing device (e.g., the training module 404 of the processing device 120) may determine a first loss of the first subnet, a second loss of the second subnet and a third loss of the third subnet in the current iteration. In some embodiments, the first, second, and third losses may be determined based on respective loss functions. Exemplary loss functions may include a relative error (RE) loss function, a mean absolute error (MAE) loss function, a focal loss function, a log loss function, a cross-entropy loss function, a Dice loss function, etc. In some embodiments, at least one of the first loss function, the second loss function, and the third loss function may include a focal loss function. For example, a first focal loss function can be selected as the first loss function, a second focal loss function may be selected as the second loss function, a relative error loss function may be selected as the third loss function.

As described in Mingqing Zhang et al. entitled "Multi-Task Convolutional Neural Network for Joint Bone Age Assessment and Ossification Center Detection from Hand Radiograph," the contents of which are hereby incorporated by reference, the first, second, and third loss functions may be defined as exemplified in Equations (5)-(7). The first loss function $L_{cla}$ may be defined as follows:

$$L_{cla}(L_c, \hat{L}_c) = 1/N \Sigma_{i=1}^{N} \Sigma_{j=0}^{1} -L_c(i,j)(1-\hat{L}_c(i,j))^{\gamma} \log \hat{L}_c(i,j), \quad (5)$$

where $L_c$ represents a label derived from a landmark ground truth L, $\hat{L}_c$ represents a predicted classification result from the first subnet, and N represents the number (or count) of landmarks (i.e., ossification centers) to be recognized, such as 20.

The second loss function $L_{loc}$ may be defined as follows:

$$L_{loc}(H, \hat{H}) = 1/2MN \Sigma_{(x,y) \in C}^{2M} \Sigma_{i=0}^{N} -H(i,x,y)(1-\hat{H}(i,x,y))^{\gamma} \log(\hat{H}(i,x,y)), \quad (6)$$

where H represents target probability maps (one-hot coding at channel-level) derived from the landmark ground truth L, $\hat{H}$ represents predicted probability maps from the intermediate second subnet, N represents the number (or count) of landmarks (i.e., ossification centers) to be recognized, M represents the number (or count) of elements in the coordinate set of positive samples for all landmarks or the counterpart of negative samples, and C represents a union set of the coordinate sets of the positive samples and the negative samples. In some embodiments, in a training sample (e.g., a hand radiograph), for the i-th landmark, if the landmark appears, it and its neighboring pixels (e.g., whose Euclidean distance from the pixel is less than 3 pixels) may be set to be indexes to positive samples, and the rest pixels are the counterpart of the positive samples.

The third loss function $L_{BAA}$ may be defined as follows:

$$L_{BAA}(B, \hat{B}) = \frac{|B - \hat{B}|}{B}, \quad (7)$$

where B represents the bone age ground truth, and $\hat{B}$ represents an estimated bone age from the third subnet.

According to the first loss function, the second loss function, and the third loss function, the processing device 120 may determine the first loss, the second loss, and the third loss. It should be noted that any suitable loss function may be adopted according to the training goals and not intended to be limited to the exemplary loss functions described in the present disclosure.

In 2705, the processing device (e.g., the training module 404 of the processing device 120) may determine a total loss based on the determined first, second, and third losses. In some embodiments, the total loss function of the multi-task network model may be a linear combination of the loss functions of the first, second and third subnets. For example, the total loss function $L_{MU}$ may be defined as follows:

$$L_{MU}(B,L,\hat{B},\hat{L}) = \alpha_1 L_{BAA}(B,\hat{B}) + \alpha_2 L_{cla}(L_c,\hat{L}_c) + \alpha_3 L_{loc}(H,\hat{H}), \quad (8)$$

where $\alpha_1$, $\alpha_2$, and $\alpha_3$ represent a weight factor of the first loss, the second loss, and the third loss, respectively. In some embodiments, the weight factors may be equal or different. For example, if the OCD and the BAA are deemed of equal importance, $\alpha_1 = \alpha_2 = \alpha_3 = 0.5$. The processing device 120 may determine the total loss based on Equation (8).

In 2706, the processing device (e.g., the training module 404 of the processing device 120) may determine whether a termination condition is satisfied. If the termination condition is satisfied, the processing device 120 may proceed to operation 2708 and complete the iterative process. If the termination condition is not satisfied, the processing device may proceed to operation 2707 and perform a next iteration. The termination condition may provide an indication of whether the multi-task network model is sufficiently trained.

In some embodiments, the termination condition may be satisfied if the total loss is equal to or less than a threshold (e.g., a constant). In some embodiments, the termination condition may be satisfied if the total loss converges. For example, the total loss may be converged when the variation of the total losses (e.g., the value of the loss function) in two or more consecutive iterations is equal to or less than a threshold (e.g., a constant). In some embodiments, the termination condition may be satisfied when a specified iteration number (or count), such as a maximum iteration count, is performed in the training process.

In 2707, the processing device (e.g., the training module 404 of the processing device 120) may update the parameters of the intermediate multi-task network model. In some embodiments, the processing device 120 may synchronously update at least one learning parameter of the intermediate multi-task network model using a back-propagation (BP) algorithm. Exemplary BP algorithms may include a stochastic gradient descent (SGD) algorithm, an Adam algorithm, an Adagrad algorithm, an Adadelta algorithm, an RMSprop algorithm, or the like, or a combination thereof. For example, the training module 404 may update the parameters using the SGD algorithm.

In 2708, the processing device (e.g., the training module 404 of the processing device 120) may determine the multi-task network model. In some embodiments, the multi-task network model may be determined based on the updated parameters. The iterative process may terminate. The trained multi-task network model may be invoked to classify, localize the ossification centers, and estimate the bone age of the subject.

In some embodiments, process 2700 may be repeated with respect to the plurality of training samples to improve or optimize the multi-task network model until the termination condition is satisfied. In different rounds of process 2700, different training samples may be inputted into an intermediate multi-task network model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 28:
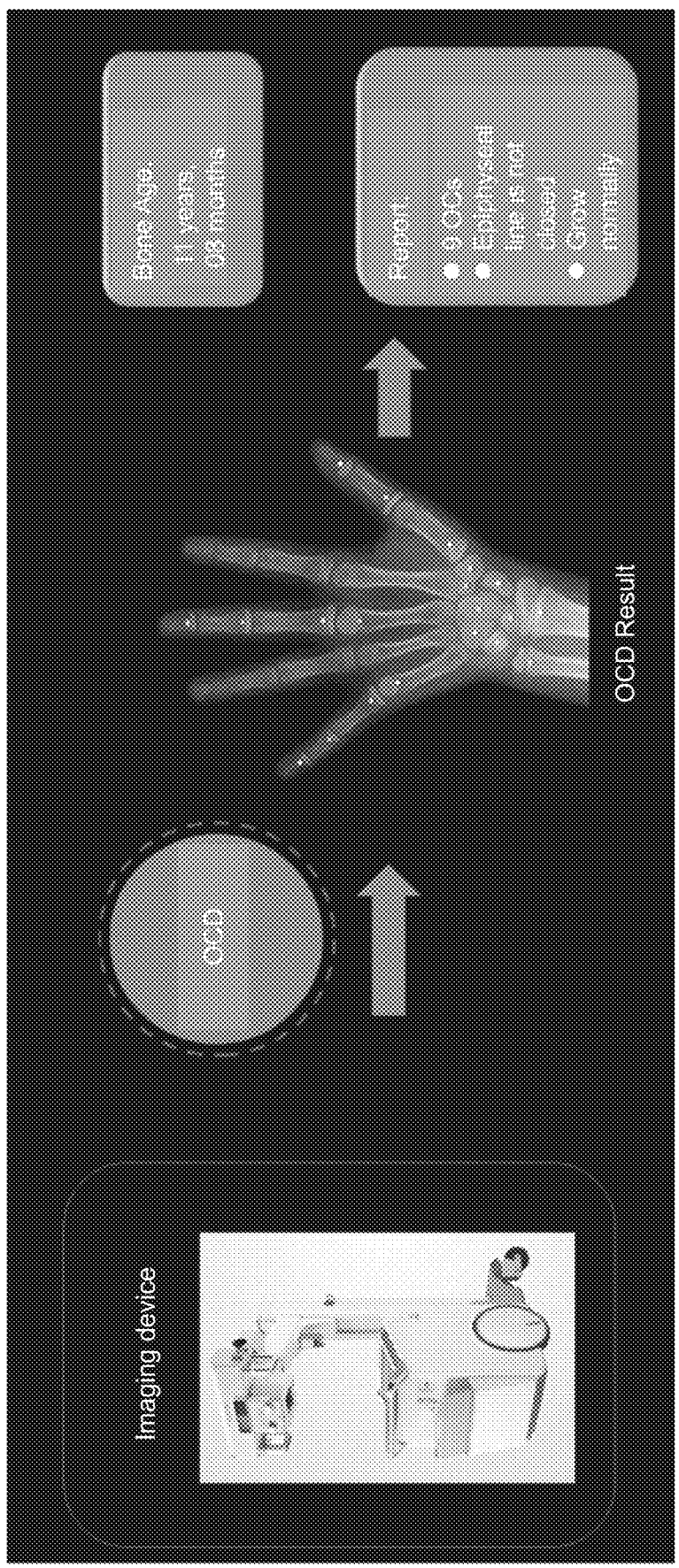
FIG. 28 illustrates an exemplary clinical application of an image processing system according to some embodiments of the present disclosure.

FIG. 28 illustrates an exemplary clinical application of the image processing system 100 according to some embodiments of the present disclosure. The imaging processing system 100 may be a fully automated ossification center detection (OCD) and bone age assessment (BAA) system with automated report generation. As illustrated in FIG. 28, an imaging device (e.g., an X-ray scanner) may be configured to scan a bone region of a subject and generate a bone age image (e.g., a hand radiograph). The image processing system 100 may process the bone age image using one or more models described in the present disclosure (e.g., the OCL model, the BAA model and/or the multi-task network model). For example, the image processing system 100 may produce an OCD result using the OCL model. The OCD result may include ossification center classification and/or localization results. According to the OCD result, the imaging processing system 100 may predict the bone age using the BAA model. As another example, the image processing system 100 may perform the OCD and the BAA simultaneously using the multi-task network model. In some embodiments, the image processing system 100 may generate a standardized report based on the OCD and the BAA results, such as the BAA report or the GA report. By using the imaging processing system 100, the diagnostic accuracy and efficiency may be improved than conventional medical measures (e.g., G&P or TW2).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device having at least one processor and at least one storage device, comprising:
    obtaining a bone age image of a subject;
    generating a normalized bone age image by preprocessing the bone age image;
    determining, based on the normalized bone age image, positions of a plurality of ossification centers using an ossification center determination model; and
    marking the positions of the plurality of ossification centers on the normalized bone age image.

2. The method of claim 1, wherein the ossification center determination model is an ossification center localization (OCL) model.

3. The method of claim 2, further comprising:
    estimating, based on the normalized bone age image and information relating to the positions of the plurality of ossification centers, a bone age of the subject using a bone age assessment (BAA) model.

4. The method of claim 3, further comprising:
    generating a report based on characteristic information of the subject, the positions of the plurality of ossification centers, or the bone age.

5. The method of claim 3, wherein
    the BAA model includes a first part and a second part, and
    the estimating, based on the normalized bone age image and information relating to the positions of the plurality of ossification centers, a bone age of the subject using a bone age assessment (BAA) model further includes:
        inputting the normalized bone age image and the information relating to the positions of the plurality of ossification centers to the first part of the BAA model;
        obtaining gender information of the subject; and
        estimating the bone age of the subject by feeding outputs of the first part of the BAA model and the gender information to the second part of the BAA model.

6. The method of claim 3, wherein
    the OCL model and the BAA model are jointly trained based on a plurality of training samples and a total loss function, and
    the total loss function includes a linear combination of respective loss functions of the OCL model and the BAA model.

7. The method of claim 2, wherein
    the plurality of ossification centers include a plurality of primary ossification centers and a plurality of secondary ossification centers,
    the OCL model includes a first OCL sub-model and a second OCL sub-model, and
    the determining, based on the normalized bone age image, positions of the plurality of ossification centers using an OCL model further includes:
        determining positions of the plurality of secondary ossification centers using the first OCL sub-model; and
        determining, based on the positions of the plurality of secondary ossification centers, positions of the plurality of primary ossification centers using the second OCL sub-model.

8. The method of claim 7, wherein
    the first OCL sub-model outputs a first batch of probability maps each of which corresponds to a position of one of the plurality of secondary ossification centers, and
    the second OCL sub-model outputs a second batch of probability maps each of which corresponds to a position of one of the plurality of primary ossification centers.

9. The method of claim 7, wherein the determining, based on the positions of the plurality of secondary ossification centers, positions of the plurality of primary ossification centers using the second OCL sub-model further includes:

generating, based on at least part of the positions of the plurality of secondary ossification centers, a region of interest (ROI) image from the normalized bone age image; and determining, based on the ROI image, the positions of the plurality of primary ossification centers using the second OCL sub-model.

10. The method of claim 9, wherein the generating, based on at least part of the positions of the plurality of secondary ossification centers, a region of interest (ROI) image from the normalized bone age image further includes:

designating one or more of the positions of the plurality of secondary ossification centers as positioning points; and generating the ROI image based on the positioning points.

11. The method of claim 7, wherein the determining, based on the positions of the plurality of secondary ossification centers, positions of the plurality of primary ossification centers using the second OCL sub-model further includes:

generating a high-resolution image corresponding to the ROI image using an interpolation algorithm;

inputting the high-resolution image to the second OCL sub-model; and determining the positions of the plurality of primary ossification centers based on outputs of the second OCL sub-model.

12. The method of claim 1, wherein the ossification center determination model is a multi-task network model, and the method includes:

performing, based on the normalized bone age image, a bone age assessment (BAA) and an ossification center detection (OCD) simultaneously using the multi-task network model.

13. The method of claim 12, wherein the OCD includes a classification and a localization for the plurality of ossification centers, and the multi-task network model includes a first subnet configured to classify the plurality of ossification centers, a second subnet configured to localize positions of the plurality of ossification centers, and a third subnet configured to assess a bone age of the subject.

14. The method of claim 13, wherein the multi-task network model further includes a backbone network connected to at least one of the first subnet, the second subnet, and the third subnet.

15. The method of claim 14, wherein the performing, based on the normalized bone age image, a bone age assessment (BAA) and an ossification center detection (OCD) simultaneously using a multi-task network model further includes:

obtaining one or more first feature maps generated by a contracting path of the backbone network; and classifying the plurality of ossification centers by inputting the one or more first feature maps to the first subnet.

16. The method of claim 15, wherein the performing, according to the normalized bone age image, a bone age assessment (BAA) and an ossification center detection (OCD) simultaneously using a multi-task network model further includes:

obtaining one or more second feature maps generated by an expanding path of the backbone network, wherein the second feature maps are generated based on the one or more first feature maps; and localizing the positions of the plurality of ossification centers by inputting the one or more second feature maps to the second subnet.

17. The method of claim 16, wherein the performing, according to the normalized bone age image, a bone age assessment (BAA) and an ossification center detection (OCD) simultaneously using a multi-task network model further includes:

obtaining one or more third feature maps generated by one or more stages of the expanding path of the backbone network, the one or more third feature maps including the one or more first feature maps and the one or more second feature maps;

obtaining gender information of the subject; and estimating the bone age of the subject by feeding the one or more third feature maps and the gender information to the third subnet.

18. The method of claim 12, wherein the multi-task network model is trained based on a plurality of training samples and a total loss function, and the total loss function is a linear combination of respective loss functions of the first subnet, the second subnet, and the third subnet.

19. A system, comprising:

at least one storage device including a set of instructions; and at least one processor configured to communicate with the at least one storage device, wherein when executing the set of instructions, the at least one processor is configured to direct the system to perform operations including:

obtaining a bone age image of a subject;

generating a normalized bone age image by preprocessing the bone age image;

determining, based on the normalized bone age image, positions of a plurality of ossification centers using an ossification center determination model; and marking the positions of the plurality of ossification centers on the normalized bone age image.

20. A non-transitory computer-readable medium, comprising at least one set of instructions, wherein when executed by at least one processor of a computer device, the at least one set of instructions directs the at least one processor to perform operations including:

obtaining a bone age image of a subject;

generating a normalized bone age image by preprocessing the bone age image;

determining, based on the normalized bone age image, positions of a plurality of ossification centers using an ossification center determination model; and marking the positions of the plurality of ossification centers on the normalized bone age image.

* * * * *